United States Patent

Mattox

Patent Number: 5,594,017
Date of Patent: Jan. 14, 1997

[54] STABILIZATION OF AQUEOUS 3-ISOTHIAZOLONE SOLUTIONS

[75] Inventor: John R. Mattox, Perkasie, Pa.

[73] Assignee: Rohm and Haas Company, Philadelphia, Pa.

[21] Appl. No.: 450,190

[22] Filed: May 25, 1995

[51] Int. Cl.$^6$ .......................... A01N 43/80; C07D 275/03
[52] U.S. Cl. ........................................... 514/372; 548/213
[58] Field of Search ............................. 514/372; 548/213

[56] References Cited

U.S. PATENT DOCUMENTS

| | | | |
|---|---|---|---|
| Re. 34,185 | 2/1993 | Amick | 548/213 |
| 4,906,274 | 3/1990 | Mattox | 548/213 X |
| 5,153,213 | 10/1992 | Schmidt | 514/372 |

Primary Examiner—Richard L. Raymond
Attorney, Agent, or Firm—Julie J. L. Cheng

[57] ABSTRACT

Compositions comprising water, microbicidally active 3-isothiazolone compound, and an effective stabilizing amount of unsaturated, cyclic iodosyl or iodyl compound of formula I and II

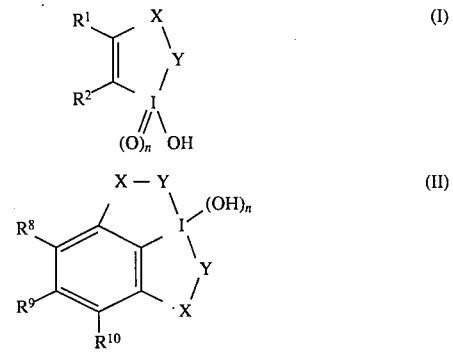

wherein:

$X=C(O)$, $SO_2$, $OPO_3H$, $CH_2C(O)$;

$Y=O$, $NR^3$;

$R^1$=H, Cl, Br, I, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;

$R^2$=H, Cl, Br, I, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl, $SO_3H$, $CO_2R^4$, $C(O)NR^5R^6$;

$R^1$ and $R^2$ may by joined to form a substituted or unsubstituted 5 or 6 membered ring, optionally fused to another 5 or 6 membered aromatic ring;

$R^3$=H, $C(O)R^7$, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;

$R^4$=H, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl, $(CH_2CH_2)_p$—OH, M;

$R^5$=H, substituted or unsubstituted $C_1$–$C_{18}$ alkyl, $CH_2CH_2SO_3H$, $CH_2CH_2SO_3M$;

$R^6$=H, substituted or unsubstituted $C_1$–$C_{18}$ alkyl;

$R^7$=H, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;

$R^8$, $R^9$, $R^{10}$ are independently selected from the group consisting of CN, OH, $C_1$–$C_4$ alkyl, $C_1$–$C_4$ alkoxy, Cl, Br, F, $NO_2$, $SO_3H$, $SO_3M$, $OCH_2CH_2N^+R^6_3\ X^-$, $CO_2H$, $CO_2M$, $OPO_3H$;

M=a monovalent or divalent metal cation;

X=halogen;

n=0, 1; and p=1–30, are disclosed. Also disclosed are methods of stabilizing a microbicidally active 3-isothiazolone in a water solution comprising introducing an effective stabilizing amount of unsaturated, cyclic iodosyl or iodyl compound of formula I and II.

9 Claims, No Drawings

STABILIZATION OF AQUEOUS 3-ISOTHIAZOLONE SOLUTIONS

This invention relates to the stabilization of aqueous solutions of 3-isothiazolones.

Certain 3-isothiazolone compounds are well known microbicides. Among these are mixtures of 5-chloro-2-methyl-3-isothiazolone (or 5-chloro-2-methyl-4-isothiazolin-3-one or "CMI"); 2-methyl-3-isothiazolone (or 2-methyl-4-isothiazolin-3-one or "MI"); and 2-octyl-3-isothiazolone (or 2-n-octyl-4-isothiazolin-3-one or "OI"). These compounds are inherently unstable and commercial products require the use of a stabilizer.

The most prevalent stabilizer for aqueous solutions of mixtures of CMI and MI is magnesium nitrate. Typical 14% concentrates of mixtures of CMI and MI are stabilized with 16% magnesium nitrate, while typical dilute solutions (0.5–5% in water) of CMI and MI are stabilized either with 23% magnesium nitrate or magnesium nitrate with additional copper salt stabilizers. These high levels of stabilization salts often cause problems in certain loci, such as shock in latexes.

One solution to this problem is to use an organic stabilizer. U.S. Pat. No. 4,906,274 discloses orthoesters as stabilizers for 3-isothiazolone compounds. While these stabilizers work well for organic systems, the orthoesters hydrolyze when used in an aqueous system, thereby losing their stabilizing effect. U.S. Pat. No. RE 34,185 discloses the use of hydroxylic solvents as stabilizers. These stabilizers also work well, but again lose their stabilizing effect when used in an aqueous system.

U.S. Pat. No. 5,153,213 discloses stabilizing dilute solutions 3-isothiazolone compounds with the oxidizing agents hydrogen peroxide or sodium perborate.

I have discovered a method of stabilizing aqueous solutions of 3-isothiazolone compounds comprising introducing a stabilizing amount of an unsaturated, cyclic iodosyl or iodyl compound of formula (I) or (II):

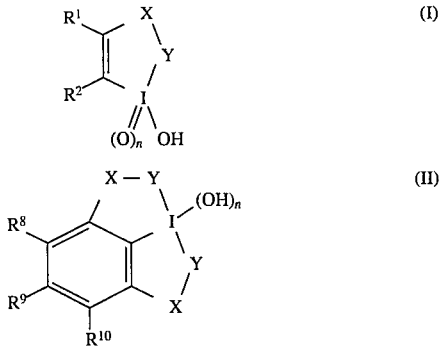

wherein:
X=C(O), $SO_2$, $OPO_3H$, $CH_2C(O)$;
Y=O, $NR^3$;
$R^1$=H, Cl, Br, I, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;
$R^2$=H, Cl, Br, I, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl, $SO_3H$, $CO_2R^4$, $C(O)NR^5R^6$;
$R^1$ and $R^2$ may by joined to form a substituted or unsubstituted 5 or 6 membered ring, optionally fused to another 5 or 6 membered aromatic ring;
$R^3$=H, $C(O)R^7$, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;
$R^4$=H, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl, $(CH_2CH_2)_p$—OH, M;
$R^5$=H, substituted or unsubstituted $C_1$–$C_{18}$ alkyl, $CH_2CH_2SO_3H$, $CH_2CH_2SO_3M$;
$R^6$=H, substituted or unsubstituted $C_1$–$C_{18}$ alkyl;
$R^7$=H, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;
$R^8$, $R^9$, $R^{10}$ are independently selected from the group consisting of CN, OH, $C_1$–$C_4$ alkyl, $C_1$–$C_4$ alkoxy, Cl, Br, F, $NO_2$, $SO_3H$, $SO_3M$, $OCH_2CH_2N^+R^6{}_3$ $X^-$, $CO_2H$, $CO_2M$, $OPO_3H$;
M=a monovalent or divalent metal cation;
X=halogen;
n=0, 1; and
p=1–30.

I have found that compositions comprising said 3-isothiazolone(s), water, and a small amount of said iodoso or iodosyl compounds are extraordinarily stable in that the 3-isothiazolone remains biocidally active and effective.

The 3-isothiazolone compounds to which this invention is most applicable are MI, CMI, and OI, especially CMI and MI, either individually or in admixture. When in admixture, the preferred ratio of chlorinated to unchlorinated 3-isothiazolone compound is from about 90:10 to 2:98 and especially preferred is a ratio of 3:1 to 4:1. Another mixture to which this invention is especially suitable for use in certain loci, such as latex or paint, comprises MI and OI.

By substituted $C_1$–$C_{18}$ alkyl is meant a $C_1$–$C_{18}$ alkyl group having one or more of its hydrogens replaced by another substituent group. Examples of suitable substituent groups include, for example, halo, cyano, nitro, $C_1$–$C_3$ alkoxy, $C_1$–$C_3$ alkylthio, $CO_2H$, $CO_2M$, $SO_3H$, $OPO_3H$, hydroxy, amino, and $C_1$–$C_{10}$ trialkylamino.

By substituted $C_2$–$C_{18}$ alkenyl is meant a $C_2$–$C_{18}$ alkenyl group having one or more of its hydrogens replaced by another substituent group. Examples of suitable substituent groups include, for example, halo, cyano, nitro, $C_1$–$C_3$ alkoxy, $C_1$–$C_3$ alkylthio, $CO_2H$, $CO_2M$,, $SO_3H$, $OPO_3H$, hydroxy, amino, and $C_1$–$C_{10}$ trialkylamino.

By substituted $C_5$–$C_6$ aryl is meant a $C_5$–$C_6$ aryl group, such as benzene, pyridine, thiophene, furan, and pyrrole, having one or more of its hydrogens replaced by another substituent group. Examples of suitable substituent groups include, for example, halo, cyano, nitro, $C_1$–$C_3$ alkoxy, $C_1$–$C_3$ alkylthio, $CO_2H$, $CO_2M$,, $SO_3H$, $OPO_3H$, hydroxy, sulfamoyl, amino, and $C_1$–$C_{10}$ trialkylamino.

By substituted $C_7$–$C_{10}$ aralkyl is meant a $C_7$–$C_{10}$ aralkyl group, such as benzyl and phenethyl, having one or more of its hydrogens replaced by another substituent group. Examples of suitable substituent groups include, for example, halo, cyano, nitro, $C_1$–$C_3$ alkoxy, $C_1$–$C_3$ alkylthio, $CO_2H$, $CO_2M$, $SO_3H$, $OPO_3H$, hydroxy, sulfamoyl, amino, and $C_1$–$C_{10}$ trialkylammonium.

By substituted 5 or 6 membered ring is meant any 5 or 6 membered ring, such as cyclohexene, cyclopentene, benzene, furan, dihydrofuran, pyrrole, dihydropyrrole, pyridine, morpholine, pyrimidine, and pyridone, having one or more of its hydrogens replaced by another substituent group. Examples of suitable substituent groups include, for example, halo, cyano, nitro, $C_1$–$C_3$ alkoxy, $C_1$–$C_3$ alkylthio, $CO_2H$, $CO_2M$, $SO_3H$, $OPO_3H$, hydroxy, sulfamoyl, amino, and $C_1$–$C_{10}$ trialkylammonium.

Suitable classes of stabilizing compounds include, for example, iodosylbenzoic acids, iodosylbenzenedicarboxylic acids, iodosylnaphthoic acids, iodosylnaphthalenedicarboxylic acids, iodosylbenzenesulfonic acids, iodosylbenzenedihydrogenphosphates, iodosylbenzamides, iodosylpyridinium carboxylates, iodosylbenzenediacetic acids, iodosylbenzeneacetic acids, iodosylsulfobenzoic acids, iodosylsulfobenzenedicarboxylic acids, iodosylsulfonaphthoic acids, and cis-3-iodosylacrylic acids, iodylbenzoic acids, iodylbenzenedicarboxylic acids, iodylnaphthoic acids, iodylnaphthalenedicarboxylic acids, iodylbenzenesulfonic acids, iodylbenzenedihydrogenphosphates, iodylbenzamides, iodylpyridinium carboxylates, iodylbenzenediacetic acids, iodylbenzeneacetic acids, iodylsulfobenzoic acids, iodylsulfobenzenedicarboxylic acids, iodylsulfonaphthoic acids, and cis-3-iodylacrylic acids, and their acid salts.

Suitable stabilizers include, for example,
2-iodosyl-1-naphthoic acid
2-iodosyl-5-methyl-1-napthoic acid
2-iodosyl-5-octadecyl-1-napthoic acid
2-iodosyl-5-phenyl-1-napthoic acid
2-iodosyl-3,5-dimethyl-1-napthoic acid
2-iodosyl-3,5-dioctadecyl-1-napthoic acid
2-iodosyl-3,5,6-trimethyl-1-napthoic acid
2-iodosyl-3,5,6-trioctadecyl-1-napthoic acid
2-iodosyl-3,4,5,6-tetramethyl-1-napthoic acid
2-iodosyl-3,4,5,6-tetraoctyl-1-napthoic acid
2-iodosyl-5-nitro-1-napthoic acid
2-iodosyl-5-chloro-1-napthoic acid
2-iodosyl-5-bromo-1-napthoic acid
2-iodosyl-5-methoxy-1-napthoic acid
2-iodosyl-3-octadecyloxy-1-napthoic acid
2-iodosyl-5-hydroxy-1-napthoic acid
2-iodosyl-3,5-dihydroxy-1-napthoic acid
2-iodosyl-5-sulfo-1-napthoic acid
2-iodosyl-3,5-disulfo-1-napthoic acid
2-iodosyl-5-[2-(2-methoxyethoxy)ethoxy]-1-napthoic acid
2-iodosyl-3,5-dinitro-1-napthoic acid
2-iodosyl-3,5-dichloro-1-napthoic acid
2-iodosyl-3,5-dibromo-1-napthoic acid
2-iodosyl-3-iodo-1-napthoic acid
2-iodosyl-3,5-diiodo-1-napthoic acid
2-iodosyl-5-(2-hydroxyethoxy)-1-napthoic acid
2-iodosyl--5-omega-hydroxypoly(oxyethylene)-1-napthoic acid
2-iodosyl-3,5-diphenyl-1-napthoic acid
2-iodosyl-3,5,6-triphenyl-1-napthoic acid
2-iodosyl-3-acetyl-1-napthoic acid
2-iodosyl-3-octadecanoyl-1-napthoic acid
2-iodosyl-5-cyclohexyl-1-napthoic acid
2-iodosyl-5-(octadec-7-enyl)-1-napthoic acid
2-iodosyl-3-propargyl-1-napthoic acid
2-iodosyl-5-fluoro-1-napthoic acid
2-iodosyl-3,5-difluoro-1-napthoic acid
2-iodosyl-5-trifluoromethyl-1-napthoic acid
2-iodosyl-3,5-ditrifluoromethyl-1-napthoic acid
2-iodosyl-3,5,6-trichloro-1-napthoic acid
2-iodosyl-3-trifluoromethoxy-1-napthoic acid
1-iodosyl-2-naphthoic acid
1-iodosyl-5-methyl-2-naphthoic acid
1-iodosyl-5-octadecyl-2-naphthoic acid
1-iodosyl-5-phenyl-2-naphthoic acid
1-iodosyl-3,5-dimethyl-2-naphthoic acid
1-iodosyl-3,5-dioctadecyl-2-naphthoic acid
1-iodosyl-3,5,6-trimethyl-2-naphthoic acid
1-iodosyl-3,5,6-trioctadecyl-2-naphthoic acid
1-iodosyl-3,4,5,6-tetramethyl-2-naphthoic acid
1-iodosyl-3,4,5,6-tetraoctyl-2-naphthoic acid
1-iodosyl-5-nitro-2-naphthoic acid
1-iodosyl-5-chloro-2-naphthoic acid
1-iodosyl-5-bromo-2-naphthoic acid
1-iodosyl-5-methoxy-2-naphthoic acid
1-iodosyl-3-octadecyloxy-2-naphthoic acid
1-iodosyl-5-hydroxy-2-naphthoic acid
1-iodosyl-3,5-dihydroxy-2-naphthoic acid
1-iodosyl-5-sulfo-2-naphthoic acid
1-iodosyl-3,5-disulfo-2-naphthoic acid
1-iodosyl-5-[2-(2-methoxyethoxy)ethoxy]-2-naphthoic acid
1-iodosyl-3,5-dinitro-2-naphthoic acid
1-iodosyl-3,5-dichloro-2-naphthoic acid
1-iodosyl-3,5-dibromo-2-naphthoic acid
1-iodosyl-3-iodo-2-naphthoic acid
1-iodosyl-3,5-diiodo-2-naphthoic acid
1-iodosyl-5-(2-hydroxyethoxy)-2-naphthoic acid
1-iodosyl-5-omega-hydroxy poly(oxyethylene)-2-naphthoic acid
1-iodosyl-3,5-diphenyl-2-naphthoic acid
1-iodosyl-3,5,6-triphenyl-2-naphthoic acid
1-iodosyl-3-acetyl-2-naphthoic acid
1-iodosyl-3-octadecanoyl-2-naphthoic acid
1-iodosyl-5-cyclohexyl-2-naphthoic acid
1-iodosyl-5-(octadec-7-enyl)-2-naphthoic acid
1-iodosyl-3-propargyl-2-naphthoic acid
1-iodosyl-5-fluoro-2-naphthoic acid
1-iodosyl-3,5-difluoro-2-naphthoic acid
1-iodosyl-5-trifluoromethyl-2-naphthoic acid
1-iodosyl-3,5-ditrifluoromethyl-2-naphthoic acid
1-iodosyl-3,5,6-trichloro-2-naphthoic acid
1-iodosyl-3-trifluoromethoxy-2-naphthoic acid
2-iodosyl-benzene sulfonic acid
2-iodosyl-5-methylbenzene sulfonic acid
2-iodosyl-5-octadecylbenzene sulfonic acid
2-iodosyl-5-phenylbenzene sulfonic acid
2-iodosyl-3,5-dimethylbenzene sulfonic acid
2-iodosyl-3,5-dioctadecylbenzene sulfonic acid
2-iodosyl-3,5,6-trimethylbenzene sulfonic acid
2-iodosyl-3,5,6-trioctadecylbenzene sulfonic acid
2-iodosyl-3,4,5,6-tetramethylbenzene sulfonic acid
2-iodosyl-3,4,5,6-tetraoctylbenzene sulfonic acid
2-iodosyl-5-nitrobenzene sulfonic acid
2-iodosyl-5-chlorobenzene sulfonic acid
2-iodosyl-5-bromobenzene sulfonic acid
2-iodosyl-5-methoxybenzene sulfonic acid
2-iodosyl-3-octadecyloxybenzene sulfonic acid
2-iodosyl-5-hydroxybenzene sulfonic acid
2-iodosyl-3,5-dihydroxybenzene sulfonic acid
2-iodosyl-5-sulfobenzene sulfonic acid
2-iodosyl-3,5-disulfobenzene sulfonic acid
2-iodosyl-5-[2-(2-methoxyethoxy)ethoxy]benzene sulfonic acid
2-iodosyl-3,5-dinitrobenzene sulfonic acid
2-iodosyl-3,5-dichlorobenzene sulfonic acid
2-iodosyl-3,5-dibromobenzene sulfonic acid
2-iodosyl-3-iodobenzene sulfonic acid
2-iodosyl-3,5-diiodobenzene sulfonic acid
2-iodosyl-5-(2-hydroxyethoxy)benzene sulfonic acid
2-iodosyl-5-omega-hydroxypoly(oxyethylene)benzene sulfonic acid
2-iodosyl-3,5-diphenylbenzene sulfonic acid
2-iodosyl-3,5,6-triphenylbenzene sulfonic acid
2-iodosyl-3-acetylbenzene sulfonic acid
2-iodosyl-3-octadecanoylbenzene sulfonic acid
2-iodosyl-5-(octadec-7-enyl)benzene sulfonic acid
2-iodosyl-3-propargylbenzene sulfonic acid
2-iodosyl-5-fluorobenzene sulfonic acid
2-iodosyl-3,5-difluorobenzene sulfonic acid
2-iodosyl-5-trifluoromethylbenzene sulfonic acid
2-iodosyl-3,5-ditrifluoromethylbenzene sulfonic acid
2-iodosyl-3,5,6-trichlorobenzene sulfonic acid
2-iodosyl-3-trifluoromethoxybenzene sulfonic acid
2-iodosyl-5-cyclohexylbenzene sulfonic acid
2-iodosyl-phenol dihydrogen phosphate
2-iodosyl-5-methylphenol dihydrogen phosphate
2-iodosyl-5-octadecylphenol dihydrogen phosphate
2-iodosyl-5-phenylphenol dihydrogen phosphate
2-iodosyl-3,5-dimethylphenol dihydrogen phosphate
2-iodosyl-3,5-dioctadecylphenol dihydrogen phosphate 2-iodosyl-3,5,6-trimethylphenol dihydrogen phosphate
2-iodosyl-3,5,6-trioctadecylphenol dihydrogen phosphate
2-iodosyl-3,4,5,6-tetramethylphenol dihydrogen phosphate
2-iodosyl-3,4,5,6-tetraoctylphenol dihydrogen phosphate
2-iodosyl-5-nitrophenol dihydrogen phosphate
2-iodosyl-5-chlorophenol dihydrogen phosphate
2-iodosyl-5-bromophenol dihydrogen phosphate
2-iodosyl-5-methoxyphenol dihydrogen phosphate
2-iodosyl-3-octadecyloxyphenol dihydrogen phosphate
2-iodosyl-5-hydroxyphenol dihydrogen phosphate
2-iodosyl-3,5-dihydroxyphenol dihydrogen phosphate
2-iodosyl-5-sulfophenol dihydrogen phosphate
2-iodosyl-3,5-disulfophenol dihydrogen phosphate
2-iodosyl-5-[2-(2-methoxyethoxy)ethoxy]phenol dihydrogen phosphate
2-iodosyl-3,5-dinitrophenol dihydrogen phosphate
2-iodosyl-3,5-dichlorophenol dihydrogen phosphate
2-iodosyl-3,5-dibromophenol dihydrogen phosphate
2-iodosyl-3-iodophenol dihydrogen phosphate
2-iodosyl-3,5-diiodophenol dihydrogen phosphate
2-iodosyl-5-(2-hydroxyethoxy)phenol dihydrogen phosphate
2-iodosyl--5-omega-hydroxypoly(oxyethylene)phenol dihydrogen phosphate
2-iodosyl-3,5-diphenylphenol dihydrogen phosphate
2-iodosyl-3,5,6-triphenylphenol dihydrogen phosphate
2-iodosyl-3-acetylphenol dihydrogen phosphate
2-iodosyl-3-octadecanoylphenol dihydrogen phosphate
2-iodosyl-5-cyclohexylphenol dihydrogen phosphate
2-iodosyl-5-(octadec-7-enyl)phenol dihydrogen phosphate
2-iodosyl-3-propargylphenol dihydrogen phosphate
2-iodosyl-5-fluorophenol dihydrogen phosphate
2-iodosyl-3,5-difluorophenol dihydrogen phosphate
2-iodosyl-3,5-ditrifluoromethylphenol dihydrogen phosphate
2-iodosyl-3,5,6-trichlorophenol dihydrogen phosphate
2-iodosyl-3-trifluoromethoxyphenol dihydrogen phosphate
2-iodosyl-N-acetylbenzamide
2-iodosyl-5-methyl-N-acetylbenzamide
2-iodosyl-5-octadecyl-N-acetylbenzamide
2-iodosyl-5-phenyl-N-acetylbenzamide
2-iodosyl-3,5-dimethyl-N-acetylbenzamide
2-iodosyl-3,5-dioctadecyl-N-acetylbenzamide
2-iodosyl-3,5,6-trimethyl-N-acetylbenzamide
2-iodosyl-3,5,6-trioctadecyl-N-acetylbenzamide
2-iodosyl-3,4,5,6-tetramethyl-N-acetylbenzamide
2-iodosyl-3,4,5,6-tetraoctyl-N-acetylbenzamide
2-iodosyl-5-nitro-N-acetylbenzamide
2-iodosyl-5-chloro-N-acetylbenzamide
2-iodosyl-5-bromo-N-acetylbenzamide
2-iodosyl-5-methoxy-N-acetylbenzamide
2-iodosyl-3-octadecyloxy-N-acetylbenzamide
2-iodosyl-5-hydroxy-N-acetylbenzamide
2-iodosyl-3,5-dihydroxy-N-acetylbenzamide
2-iodosyl-5-sulfo-N-acetylbenzamide
2-iodosyl-3,5-disulfo-N-acetylbenzamide
2-iodosyl-5-[2-(2-methoxyethoxy)ethoxy]-N-acetylbenzamide
2-iodosyl-3,5-dinitro-N-acetylbenzamide
2-iodosyl-3,5-dichloro-N-acetylbenzamide
2-iodosyl-3,5-dibromo-N-acetylbenzamide
2-iodosyl-3-iodo-N-acetylbenzamide
2-iodosyl-3,5-diiodo-N-acetylbenzamide
2-iodosyl-5-(2-hydroxyethoxy)-N-acetylbenzamide
2-iodosyl-5-omega-hydroxypoly(oxyethylene)-N-acetylbenzamide
2-iodosyl-3,5-diphenyl-N-acetylbenzamide
2-iodosyl-3,5,6-triphenyl-N-acetylbenzamide
2-iodosyl-3-acetyl-N-acetylbenzamide
2-iodosyl-3-octadecanoyl-N-acetylbenzamide
2-iodosyl-5-cyclohexyl-N-acetylbenzamide
2-iodosyl-5-(octadec-7-enyl)-N-acetylbenzamide
2-iodosyl-3-propargyl-N-acetylbenzamide
2-iodosyl-5-fluoro-N-acetylbenzamide
2-iodosyl-3,5-difluoro-N-acetylbenzamide
2-iodosyl-5-trifluoromethyl-N-acetylbenzamide
2-iodosyl-3,5-ditrifluoromethyl-N-acetylbenzamide
2-iodosyl-3,5,6-trichloro-N-acetylbenzamide
2-iodosyl-3-trifluoromethoxy-N-acetylbenzamide
2-iodosyl-N-octadecanoylbenzamide
2-iodosyl-5-methyl-N-octadecanoylbenzamide
2-iodosyl-5-octadecyl-N-octadecanoylbenzamide
2-iodosyl-5-phenyl-N-octadecanoylbenzamide
2-iodosyl-3,5-dimethyl-N-octadecanoylbenzamide
2-iodosyl-3,5-dioctadecyl-N-octadecanoylbenzamide
2-iodosyl-3,5,6-trimethyl-N-octadecanoylbenzamide
2-iodosyl-3,5,6-trioctadecyl-N-octadecanoylbenzamide
2-iodosyl-3,4,5,6-tetramethyl-N-octadecanoylbenzamide
2-iodosyl-3,4,5,6-tetraoctyl-N-octadecanoylbenzamide
2-iodosyl-5-nitro-N-octadecanoylbenzamide
2-iodosyl-5-chloro-N-octadecanoylbenzamide
2-iodosyl-5-bromo-N-octadecanoylbenzamide
2-iodosyl-5-methoxy-N-octadecanoylbenzamide
2-iodosyl-3-octadecyloxy-N-octadecanoylbenzamide
2-iodosyl-5-hydroxy-N-octadecanoylbenzamide
2-iodosyl-3,5-dihydroxy-N-octadecanoylbenzamide
2-iodosyl-5-sulfo-N-octadecanoylbenzamide
2-iodosyl-3,5-disulfo-N-octadecanoylbenzamide
2-iodosyl-5-[2-(2-methoxyethoxy)ethoxy]-N-octadecanoylbenzamide
2-iodosyl-3,5-dinitro-N-octadecanoylbenzamide
2-iodosyl-3,5-dichloro-N-octadecanoylbenzamide
2-iodosyl-3,5-dibromo-N-octadecanoylbenzamide
2-iodosyl-3-iodo-N-octadecanoylbenzamide
2-iodosyl-3,5-diiodo-N-octadecanoylbenzamide
2-iodosyl-5-(2-hydroxyethoxy)-N-octadecanoylbenzamide
2-iodosyl-5-omega-hydroxypoly(oxyethylene)-N-octadecanoylbenzamide
2-iodosyl-3,5-diphenyl-N-octadecanoylbenzamide
2-iodosyl-3,5,6-triphenyl-N-octadecanoylbenzamide
2-iodosyl-3-acetyl-N-octadecanoylbenzamide
2-iodosyl-3-octadecanoyl-N-octadecanoylbenzamide
2-iodosyl-5-cyclohexyl-N-octadecanoylbenzamide
2-iodosyl-5-(octadec-7-enyl)-N-octadecanoylbenzamide
2-iodosyl-3-propargyl-N-octadecanoylbenzamide
2-iodosyl-5-fluoro-N-octadecanoylbenzamide
2-iodosyl-3,5-difluoro-N-octadecanoylbenzamide
2-iodosyl-5-trifluoromethyl-N-octadecanoylbenzamide
2-iodosyl-3,5-ditrifluoromethyl-N-octadecanoylbenzamide
2-iodosyl-3,5,6-trichloro-N-octadecanoylbenzamide
2-iodosyl-3-trifluoromethoxy-N-octadecanoylbenzamide
2-iodosyl-benzenesulfamide
2-iodosyl-5-methylbenzenesulfamide
2-iodosyl-5-octadecylbenzenesulfamide
2-iodosyl-5-phenylbenzenesulfamide
2-iodosyl-3,5-dimethylbenzenesulfamide
2-iodosyl-3,5-dioctadecylbenzenesulfamide
2-iodosyl-3,5,6-trimethylbenzenesulfamide
2-iodosyl-3,5,6-trioctadecylbenzenesulfamide
2-iodosyl-3,4,5,6-tetramethylbenzenesulfamide
2-iodosyl-3,4,5,6-tetraoctylbenzenesulfamide
2-iodosyl-5-nitrobenzenesulfamide
2-iodosyl-5-chlorobenzenesulfamide
2-iodosyl-5-bromobenzenesulfamide
2-iodosyl-5-methoxybenzenesulfamide
2-iodosyl-3-octadecyloxybenzenesulfamide
2-iodosyl-5-hydroxybenzenesulfamide
2-iodosyl-3,5-dihydroxybenzenesulfamide
2-iodosyl-5-sulfobenzenesulfamide
2-iodosyl-3,5-disulfobenzenesulfamide
2-iodosyl-5-[2-(2-methoxyethoxy)ethoxy]benzenesulfamide 2-iodosyl-3,5-dinitrobenzenesulfamide
2-iodosyl-3,5-dichlorobenzenesulfamide
2-iodosyl-3,5-dibromobenzenesulfamide
2-iodosyl-3-iodobenzenesulfamide
2-iodosyl-3,5-diiodobenzenesulfamide
2-iodosyl-5-(2-hydroxyethoxy)-enzenesulfamide
2-iodosyl-5-omega-hydroxypoly(oxyethylene)-enzenesulfamide
2-iodosyl-3,5-diphenylbenzenesulfamide
2-iodosyl-3,5,6-triphenylbenzenesulfamide
2-iodosyl-3-acetylbenzenesulfamide
2-iodosyl-3-octadecanoylbenzenesulfamide
2-iodosyl-5-cyclohexylbenzenesulfamide
2-iodosyl-5-(octadec-7-enyl)benzenesulfamide
2-iodosyl-3-propargylbenzenesulfamide
2-iodosyl-5-fluorobenzenesulfamide
2-iodosyl-3,5-difluorobenzenesulfamide
2-iodosyl-5-trifluoromethylbenzenesulfamide
2-iodosyl-3,5-ditrifluoromethylbenzenesulfamide
2-iodosyl-3,5,6-trichlorobenzenesulfamide
2-iodosyl-3-trifluoromethoxybenzenesulfamide
2-iodosylbenzoic acid
2-iodosyl-5-methylbenzoic acid
2-iodosyl-5-octadecylbenzoic acid
2-iodosyl-5-phenylbenzoic acid
2-iodosyl-3,5-dimethylbenzoic acid
2-iodosyl-3,5-dioctadecylbenzoic acid
2-iodosyl-3,5,6-trimethylbenzoic acid
2-iodosyl-3,5,6-trioctadecylbenzoic acid
2-iodosyl-3,4,5,6-tetramethylbenzoic acid
2-iodosyl-3,4,5,6-tetraoctylbenzoic acid
2-iodosyl-5-nitrobenzoic acid
2-iodosyl-5-chlorobenzoic acid
2-iodosyl-5-bromobenzoic acid
2-iodosyl-5-methoxybenzoic acid
2-iodosyl-3-octadecyloxybenzoic acid
2-iodosyl-5-hydroxybenzoic acid
2-iodosyl-3,5-dihydroxybenzoic acid
2-iodosyl-5-sulfobenzoic acid
2-iodosyl-3,5-disulfobenzoic acid
2-iodosyl-5-[2-(2-methoxyethoxy)ethoxy]benzoic acid
2-iodosyl-3,5-dinitrobenzoic acid
2-iodosyl-3,5-dichlorobenzoic acid
2-iodosyl-3,5-dibromobenzoic acid
2-iodosyl-3-iodobenzoic acid
2-iodosyl-3,5-diiodobenzoic acid
2-iodosyl-5-(2-hydroxyethoxy)benzoic acid
2-iodosyl-5-omega-hydroxypoly(oxyethylene)benzoic acid
2-iodosyl-3,5-diphenylbenzoic acid
2-iodosyl-3,5,6-triphenylbenzoic acid
2-iodosyl-3-acetylbenzoic acid
2-iodosyl-3-octadecanoylbenzoic acid
2-iodosyl-5-cyclohexylbenzoic acid
2-iodosyl-5-(octadec-7-enyl)benzoic acid
2-iodosyl-3-propargylbenzoic acid
2-iodosyl-5-fluorobenzoic acid
2-iodosyl-3,5-difluorobenzoic acid
2-iodosyl-5-trifluoromethylbenzoic acid
2-iodosyl-3,5-ditrifluoromethylbenzoic acid
2-iodosyl-3,5,6-trichlorobenzoic acid
2-iodosyl-3-trifluoromethoxybenzoic acid
2-iodosyl-1,4-benzenedicarboxylic acid
2-iodosyl-5-methyl-1,4-benzenedicarboxylic acid
2-iodosyl-5-octadecyl-1,4-benzenedicarboxylic acid
2-iodosyl-5-phenyl-1,4-benzenedicarboxylic acid
2-iodosyl-3,5-dimethyl-1,4-benzenedicarboxylic acid
2-iodosyl-3,5-dioctadecyl-1,4-benzenedicarboxylic acid
2-iodosyl-3,5-trimethyl-1,4-benzenedicarboxylic acid
2-iodosyl-3,5,6-trioctadecyl-1,4-benzenedicarboxylic acid
2-iodosyl-5-nitro-1,4-benzenedicarboxylic acid
2-iodosyl-5-chloro-1,4-benzenedicarboxylic acid
2-iodosyl-5-bromo-1,4-benzenedicarboxylic acid
2-iodosyl-5-methoxy-1,4-benzenedicarboxylic acid
2-iodosyl-3-octadecyloxy-1,4-benzenedicarboxylic acid
2-iodosyl-5-hydroxy-1,4-benzenedicarboxylic acid
2-iodosyl-3,5-dihydroxy-1,4-benzenedicarboxylic acid
2-iodosyl-5-sulfo-1,4-benzenedicarboxylic acid
2-iodosyl-3,5-disulfo-1,4-benzenedicarboxylic acid
2-iodosyl-5-[2-(2-methoxyethoxy)ethoxy]-1,4-benzenedicarboxylic acid
2-iodosyl-3,5-dinitro-1,4-benzenedicarboxylic acid
2-iodosyl-3,5-dichloro-1,4-benzenedicarboxylic acid
2-iodosyl-3,5-dibromo-1,4-benzenedicarboxylic acid
2-iodosyl-3-iodo-1,4-benzenedicarboxylic acid
2-iodosyl-3,5-diiodo-1,4-benzenedicarboxylic acid
2-iodosyl-5-(2-hydroxyethoxy)-1,4-benzenedicarboxylic acid
2-iodosyl--5-omega-hydroxypoly(oxyethylene)-1,4-benzenedicarboxylic acid
2-iodosyl-3,5-diphenyl-1,4-benzenedicarboxylic acid
2-iodosyl-3,5,6-triphenyl-1,4-benzenedicarboxylic acid
2-iodosyl-3-acetyl-1,4-benzenedicarboxylic acid
2-iodosyl-3-octadecanoyl-1,4-benzenedicarboxylic acid
2-iodosyl-5-(octadec-7-enyl)-1,4-benzenedicarboxylic acid
2-iodosyl-3-propargyl-1,4-benzenedicarboxylic acid
2-iodosyl-5-fluoro-1,4-benzenedicarboxylic acid
2-iodosyl-3,5-difluoro-1,4-benzenedicarboxylic acid
2-iodosyl-5-trifluoromethyl-1,4-benzenedicarboxylic acid
2-iodosyl-3,5-ditrifluoromethyl-1,4-benzenedicarboxylic acid
2-iodosyl-3,5,6-trichloro-1,4-benzenedicarboxylic acid
2-iodosyl-3-trifluoromethoxy-1,4-benzenedicarboxylic acid
2-iodosyl-5-cyclohexyl-1,4-benzenedicarboxylic acid
4-iodosyl-1,3-benzenedicarboxylic acid
4-iodosyl-5-methyl-1,3-benzenedicarboxylic acid
4-iodosyl-5-octadecyl-1,3-benzenedicarboxylic acid
4-iodosyl-2,5-dimethyl-1,3-benzenedicarboxylic acid
4-iodosyl-2,5-dioctadecyl-1,3-benzenedicarboxylic acid
4-iodosyl-2,5,6-trimethyl-1,3-benzenedicarboxylic acid
4-iodosyl-2,5,6-trioctadecyl-1,3-benzenedicarboxylic acid
4-iodosyl-5-nitro-1,3-benzenedicarboxylic acid
4-iodosyl-2,5-dinitro-1,3-benzenedicarboxylic acid
4-iodosyl-5-fluoro-1,3-benzenedicarboxylic acid
4-iodosyl-2,5-difluoro-1,3-benzenedicarboxylic acid
4-iodosyl-5-chloro-1,3-benzenedicarboxylic acid
4-iodosyl-2,5-dichloro-1,3-benzenedicarboxylic acid
4-iodosyl-5-bromo-1,3-benzenedicarboxylic acid
4-iodosyl-2,5-dibromo-1,3-benzenedicarboxylic acid
4-iodosyl-5-iodo-1,3-benzenedicarboxylic acid
4-iodosyl-2,5-diiodo-1,3-benzenedicarboxylic acid
4-iodosyl-5-trifluoromethyl-1,3-benzenedicarboxylic acid
4-iodosyl-5-phenyl-1,3-benzenedicarboxylic acid
4-iodosyl-2,5-diphenyl-1,3-benzenedicarboxylic acid
4-iodosyl-5-methoxy-1,3-benzenedicarboxylic acid
4-iodosyl-5-octadecyloxy-1,3-benzenedicarboxylic acid
4-iodosyl-5-hydroxy-1,3-benzenedicarboxylic acid
4-iodosyl-2,5-dihydroxy-1,3-benzenedicarboxylic acid
4-iodosyl-2,5,6-trichloro-1,3-benzenedicarboxylic acid
4-iodosyl-5-cyclohexyl-1,3-benzenedicarboxylic acid
2-iodosyl-1,3-benzenedicarboxylic acid
2-iodosyl-5-methyl-1,3-benzenedicarboxylic acid
2-iodosyl-5-octadecyl-1,3-benzenedicarboxylic acid
2-iodosyl-5-phenyl--1,3-benzenedicarboxylic acid
2-iodosyl-5-cyclohexyl-1,3-benzenedicarboxylic acid
2-iodosyl-4,5-dimethyl-1,3-benzenedicarboxylic acid
2-iodosyl-4,5-dioctadecyl-1,3-benzenedicarboxylic acid
2-iodosyl-5-nitro-1,3-benzenedicarboxylic acid
2-iodosyl-4,5-dinitro-1,3-benzenedicarboxylic acid
2-iodosyl-5-fluoro-1,3-benzenedicarboxylic acid
2-iodosyl-4,5-difluoro-1,3-benzenedicarboxylic acid
2-iodosyl-5-chloro-1,3-benzenedicarboxylic acid
2-iodosyl-4,5-dichloro-1,3-benzenedicarboxylic acid 2-iodosyl-5-bromo-1,3-benzenedicarboxylic acid
2-iodosyl-4,5-dibromo-1,3-benzenedicarboxylic acid
2-iodosyl-5-iodo-1,3-benzenedicarboxylic acid
2-iodosyl-4,5-diiodo-1,3-benzenedicarboxylic acid
2-iodosyl-5-sulfo-1,3-benzenedicarboxylic acid
2-iodosyl-5-methoxy-1,3-benzenedicarboxylic acid
2-iodosyl-octadecyloxy-1,3-benzenedicarboxylic acid
2-iodosyl-5-acetyl-1,3-benzenedicarboxylic acid
2-iodosyl-5-hydroxy-1,3-benzenedicarboxylic acid
2-iodosyl-4,5-diphenyl-1,3-benzenedicarboxylic acid
2-iodosyl-4,5-dihydroxy-1,3-benzenedicarboxylic acid
2-iodosyl-5-propargyl-1,3-benzenedicarboxylic acid
2-iodosylbenzeneacetic acid
2-iodosyl-5-methylbenzeneacetic acid
2-iodosyl-5-octadecylbenzeneacetic acid
2-iodosyl-5-phenylbenzeneacetic acid
2-iodosyl-3,5-dimethylbenzeneacetic acid
2-iodosyl-3,5-dioctadecylbenzeneacetic acid
2-iodosyl-3,5,6-trimethylbenzeneacetic acid
2-iodosyl-3,5,6-trioctadecylbenzeneacetic acid
2-iodosyl-3,4,5,6-tetramethylbenzeneacetic acid
2-iodosyl-3,4,5,6-tetraoctylbenzeneacetic acid
2-iodosyl-5-nitrobenzeneacetic acid
2-iodosyl-5-chlorobenzeneacetic acid
2-iodosyl-5-bromobenzeneacetic acid
2-iodosyl-5-methoxybenzeneacetic acid
2-iodosyl-3-octadecyloxybenzeneacetic acid
2-iodosyl-5-hydroxybenzeneacetic acid
2-iodosyl-3,5-dihydroxybenzeneacetic acid
2-iodosyl-5-sulfobenzeneacetic acid
2-iodosyl-3,5-disulfobenzeneacetic acid
2-iodosyl-5-[2-(2-methoxyethoxy)ethoxy]benzeneacetic acid
2-iodosyl-3,5-dinitrobenzeneacetic acid
2-iodosyl-3,5-dichlorobenzeneacetic acid
2-iodosyl-3,5-dibromobenzeneacetic acid
2-iodosyl-3-iodobenzeneacetic acid
2-iodosyl-3,5-diiodobenzeneacetic acid
2-iodosyl-5-(2-hydroxyethoxy)benzeneacetic acid
2-iodosyl-5-omega-hydroxypoly(oxyethylene)benzeneacetic acid
2-iodosyl-3,5-diphenylbenzeneacetic acid
2-iodosyl-3,5,6-triphenylbenzeneacetic acid
2-iodosyl-3-acetylbenzeneacetic acid
2-iodosyl-3-octadecanoylbenzeneacetic acid
2-iodosyl-5-cyclohexylbenzeneacetic acid
2-iodosyl-5-(octadec-7-enyl)benzeneacetic acid
2-iodosyl-3-propargyl-enzeneacetic acid
2-iodosyl-5-fluoro-enzene cetic acid
2-iodosyl-3,5-difluorobenzeneacetic acid
2-iodosyl-5-trifluoromethylbenzeneacetic acid
2-iodosyl-3,5-ditrifluoromethylbenzeneacetic acid
2-iodosyl-3,5,6-trichlorobenzeneacetic acid
2-iodosyl-3-trifluoromethoxybenzeneacetic acid
2-iodosyl-5-cyclohexylbenzeneacetic acid
2-iodosyl-1,3-benzenediacetic acid
2-iodosyl-5-methyl-1,3-benzenediacetic acid
2-iodosyl-5-octadecyl-1,3-benzenediacetic acid
2-iodosyl-5-phenyl-1,3-benzenediacetic acid
2-iodosyl-5-cyclohexyl-1,3-benzenediacetic acid
2-iodosyl-4,5-dimethyl-1,3-benzenediacetic acid
2-iodosyl-4,5-dioctadecyl-1,3-benzenediacetic acid
2-iodosyl-5-nitro-1,3-benzenediacetic acid
2-iodosyl-5-dinitro-1,3-benzenediacetic acid
2-iodosyl-5-fluoro-1,3-benzenediacetic acid
2-iodosyl-4,5-difluoro-1,3-benzenediacetic acid
2-iodosyl-5-chloro-1,3-benzenediacetic acid
2-iodosyl-4,5-dichloro-1,3-benzenediacetic acid
2-iodosyl-5-bromo-1,3-benzenediacetic acid
2-iodosyl-4,5-dibromo-1,3-benzenediacetic acid
2-iodosyl-5-iodo-1,3-benzenediacetic acid
2-iodosyl-4,5-diiodo-1,3-benzenediacetic acid
2-iodosyl-5-sulfo-1,3-benzenediacetic acid
2-iodosyl-5-methoxy-1,3-benzenediacetic acid
2-iodosyl-octadecyloxy-1,3-benzenediacetic acid
2-iodosyl-5-acetyl-1,3-benzenediacetic acid
2-iodosyl-5-hydroxy-1,3-benzenediacetic acid
2-iodosyl-4,5-diphenyl-1,3-benzenediacetic acid
2-iodosyl-4,5-dihydroxy-1,3-benzenediacetic acid
2-iodosyl-5-propargyl-1,3-benzenediacetic acid
3-iodosyl-2-naphthoic acid
3-iodosyl-5-methyl-2-naphthoic acid
3-iodosyl-5-octadecyl-2-naphthoic acid
3-iodosyl-5-phenyl-2-naphthoic acid
3-iodosyl-4,5-dimethyl-2-naphthoic acid
3-iodosyl-4,5-dioctadecyl-2-naphthoic acid
3-iodosyl-4,5,6-trimethyl-2-naphthoic acid
3-iodosyl-4,5,6-trioctadecyl-2-naphthoic acid
3-iodosyl-4,5,6,8-tetramethyl-2-naphthoic acid
3-iodosyl-4,5,6,8-tetraoctyl-2-naphthoic acid
3-iodosyl-5-nitro-2-naphthoic acid
3-iodosyl-5-chloro-2-naphthoic acid
3-iodosyl-5-bromo-2-naphthoic acid
3-iodosyl-5-methoxy-2-naphthoic acid
3-iodosyl-6-octadecyloxy-2-naphthoic acid
3-iodosyl-5-hydroxy-2-naphthoic acid
3-iodosyl-6,7-dihydroxy-2-naphthoic acid
3-iodosyl-5-sulfo-2-naphthoic acid
3-iodosyl-6,7-disulfo-2-naphthoic acid
3-iodosyl-5-[2-(2-methoxyethoxy)ethoxy]-2-naphthoic acid
3-iodosyl-4,5-dinitro-2-naphthoic acid
3-iodosyl-4,5-dichloro-2-naphthoic acid
3-iodosyl-4,5-dibromo-2-naphthoic acid
3-iodosyl-4-iodo-2-naphthoic acid
3-iodosyl-4,5-diiodo-2-naphthoic acid
3-iodosyl-5-(2-hydroxyethoxy)-2-naphthoic acid
3-iodosyl-5-omega-hydroxypoly(oxyethylene)-2-naphthoic acid
3-iodosyl-4,5-diphenyl-2-naphthoic acid
3-iodosyl-4,5,6-triphenyl-2-naphthoic acid
3-iodosyl-5-acetyl-2-naphthoic acid
3-iodosyl-5-octadecanoyl-2-naphthoic acid
3-iodosyl-5-cyclohexyl-2-naphthoic acid
3-iodosyl-5-(octadec-7-enyl)-2-naphthoic acid
3-iodosyl-5-propargyl-2-naphthoic acid
3-iodosyl-5-fluoro-2-naphthoic acid
3-iodosyl-5,6-difluoro-2-naphthoic acid
3-iodosyl-5-trifluoromethyl-2-naphthoic acid
3-iodosyl-5,6-ditrifluoromethyl-2-naphthoic acid
3-iodosyl-5,6,7-trichloro-2-naphthoic acid
3-iodosyl-5-trifluoromethoxy-2-naphthoic acid
[2-(3-carboxy-4-iodosyl phenoxy)ethyl]triethyl ammonium chloride
N-octyl-3-iodosylpyridinium-4-carboxylate
[2-(3-carboxy-4-iodosyl phenoxyl)ethyl]trimethyl ammonium chloride
cis-3-iodosylacrylic acid
trans-2-iodosylbut-2-enedioic acid
trans-2-iodosylbut-2-enedioic acid monosodium salt
cis-2-chloro-3-iodosylacrylic acid
cis-2-sulfo-3-iodosylacrylic acid
cis-2-sulfo-3-iodosylacrylic acid monosodium salt
trans-2-methyl-3-iodosylbut-2-eneoic acid
trans-3-iodosylbut-2-eneoic acid
trans-3-iodosylundodec-2-eneoic acid
2-[N -methyl-N-(4-hydroxycarbonyl-2-iodosyl-1-oxobut-2-ene)]aminoethanesulfonic acid
2-[N-methyl-N-(4-hydroxycarbonyl-2-iodosyl-1-oxobut-2-ene)]aminoethanesulfonic acid monosodium salt
2-[N-(4-hydroxycarbonyl-2-iodosyl-1-oxobut-2-ene)]aminoethanesulfonic acid
2-[N-(4-hydroxycarbonyl-2-iodosyl-1-oxobut-2-ene)]aminoethanesulfonic acid monosodium salt 2-iodyl-1-naphthoic acid
2-iodyl-5-methyl-1-napthoic acid
2-iodyl-5-octadecyl-1-napthoic acid
2-iodyl-5-phenyl-1-napthoic acid
2-iodyl-3,5-dimethyl-1-napthoic acid
2-iodyl-3,5-dioctadecyl-1-napthoic acid
2-iodyl-3,5,6-trimethyl-1-napthoic acid
2-iodyl-3,5,6-trioctadecyl-1-napthoic acid
2-iodyl-3,4,5,6-tetramethyl-1-napthoic acid
2-iodyl-3,4,5,6-tetraoctyl-1-napthoic acid
2-iodyl-5-nitro-1-napthoic acid
2-iodyl-5-chloro-1-napthoic acid
2-iodyl-5-bromo-1-napthoic acid
2-iodyl-5-methoxy-1-napthoic acid
2-iodyl-3-octadecyloxy-1-napthoic acid
2-iodyl-5-hydroxy-1-napthoic acid
2-iodyl-3,5-dihydroxy-1-napthoic acid
2-iodyl-5-sulfo-1-napthoic acid
2-iodyl-3,5-disulfo-1-napthoic acid
2-iodyl-5-[2-(2-methoxyethoxy)ethoxy]-1-napthoic acid
2-iodyl-3,5-dinitro-1-napthoic acid
2-iodyl-3,5-dichloro-1-napthoic acid
2-iodyl-3,5-dibromo-1-napthoic acid
2-iodyl-3-iodo-1-napthoic acid
2-iodyl-3,5-diiodo-1-napthoic acid
2-iodyl-5-(2-hydroxyethoxy)-1-napthoic acid
2-iodyl--5-omega-hydroxypoly(oxyethylene)-1-napthoic acid
2-iodyl-3,5-diphenyl-1-napthoic acid
2-iodyl-3,5,6-triphenyl-1-napthoic acid
2-iodyl-3-acetyl-1-napthoic acid
2-iodyl-3-octadecanoyl-1-napthoic acid
2-iodyl-5-cyclohexyl-1-napthoic acid
2-iodyl-5-(octadec-7-enyl)-1-napthoic acid
2-iodyl-3-propargyl-1-napthoic acid
2-iodyl-5-fluoro-1-napthoic acid
2-iodyl-3,5-difluoro-1-napthoic acid
2-iodyl-5-trifluoromethyl-1-napthoic acid
2-iodyl-3,5-ditrifluoromethyl-1-napthoic acid
2-iodyl-3,5,6-trichloro-1-napthoic acid
2-iodyl-3-trifluoromethoxy-1-napthoic acid
1-iodyl-2-naphthoic acid
1-iodyl-5-methyl-2-naphthoic acid
1-iodyl-5-octadecyl-2-naphthoic acid
1-iodyl-5-phenyl-2-naphthoic acid
1-iodyl-3,5-dimethyl-2-naphthoic acid
1-iodyl-3,5-dioctadecyl-2-naphthoic acid
1-iodyl-3,5,6-trimethyl-2-naphthoic acid
1-iodyl-3,5,6-trioctadecyl-2-naphthoic acid
1-iodyl-3,4,5,6-tetramethyl-2-naphthoic acid
1-iodyl-3,4,5,6-tetraoctyl-2-naphthoic acid
1-iodyl-5-nitro-2-naphthoic acid
1-iodyl-5-chloro-2-naphthoic acid
1-iodyl-5-bromo-2-naphthoic acid
1-iodyl-5-methoxy-2-naphthoic acid
1-iodyl-3-octadecyloxy-2-naphthoic acid
1-iodyl-5-hydroxy-2-naphthoic acid
1-iodyl-3,5-dihydroxy-2-naphthoic acid
1-iodyl-5-sulfo-2-naphthoic acid
1-iodyl-3,5-disulfo-2-naphthoic acid
1-iodyl-5-[2-(2-methoxyethoxy)ethoxy]-2-naphthoic acid
1-iodyl-3,5-dinitro-2-naphthoic acid
1-iodyl-3,5-dichloro-2-naphthoic acid
1-iodyl-3,5-dibromo-2-naphthoic acid
1-iodyl-3-iodo-2-naphthoic acid
1-iodyl-3,5-diiodo-2-naphthoic acid
1-iodyl-5-(2-hydroxyethoxy)-2-naphthoic acid
1-iodyl-5-omega-hydroxy poly(oxyethylene)-2-naphthoic acid
1-iodyl-3,5-diphenyl-2-naphthoic acid
1-iodyl-3,5,6-triphenyl-2-naphthoic acid
1-iodyl-3-acetyl-2-naphthoic acid
1-iodyl-3-octadecanoyl-2-naphthoic acid
1-iodyl-5-cyclohexyl-2-naphthoic acid
1-iodyl-5-(octadec-7-enyl)-2-naphthoic acid
1-iodyl-3-propargyl-2-naphthoic acid
1-iodyl-5-fluoro-2-naphthoic acid
1-iodyl-3,5-difluoro-2-naphthoic acid
1-iodyl-5-trifluoromethyl-2-naphthoic acid
1-iodyl-3,5-ditrifluoromethyl-2-naphthoic acid
1-iodyl-3,5,6-trichloro-2-naphthoic acid
1-iodyl-3-trifluoromethoxy-2-naphthoic acid
2-iodyl-benzene sulfonic acid
2-iodyl-5-methylbenzene sulfonic acid
2-iodyl-5-octadecylbenzene sulfonic acid
2-iodyl-5-phenylbenzene sulfonic acid
2-iodyl-3,5-dimethylbenzene sulfonic acid
2-iodyl-3,5-dioctadecylbenzene sulfonic acid
2-iodyl-3,5,6-trimethylbenzene sulfonic acid
2-iodyl-3,5,6-trioctadecylbenzene sulfonic acid
2-iodyl-3,4,5,6-tetramethylbenzene sulfonic acid
2-iodyl-3,4,5,6-tetraoctylbenzene sulfonic acid
2-iodyl-5-nitrobenzene sulfonic acid
2-iodyl-5-chlorobenzene sulfonic acid
2-iodyl-5-bromobenzene sulfonic acid
2-iodyl-5-methoxybenzene sulfonic acid
2-iodyl-3-octadecyloxybenzene sulfonic acid
2-iodyl-5-hydroxybenzene sulfonic acid
2-iodyl-3,5-dihydroxybenzene sulfonic acid
2-iodyl-5-sulfobenzene sulfonic acid
2-iodyl-3,5-disulfobenzene sulfonic acid
2-iodyl-5-[2-(2-methoxyethoxy)ethoxy]benzene sulfonic acid
2-iodyl-3,5-dinitrobenzene sulfonic acid
2-iodyl-3,5-dichlorobenzene sulfonic acid
2-iodyl-3,5-dibromobenzene sulfonic acid
2-iodyl-3-iodobenzene sulfonic acid
2-iodyl-3,5-diiodobenzene sulfonic acid
2-iodyl-5-(2-hydroxyethoxy)benzene sulfonic acid
2-iodyl-5-omega-hydroxypoly(oxyethylene)benzene sulfonic acid
2-iodyl-3,5-diphenylbenzene sulfonic acid
2-iodyl-3,5,6-triphenylbenzene sulfonic acid
2-iodyl-3-acetylbenzene sulfonic acid
2-iodyl-3-octadecanoylbenzene sulfonic acid
2-iodyl-5-(octadec-7-enyl)benzene sulfonic acid
2-iodyl-3-propargylbenzene sulfonic acid
2-iodyl-5-fluorobenzene sulfonic acid
2-iodyl-3,5-difluorobenzene sulfonic acid
2-iodyl-5-trifluoromethylbenzene sulfonic acid
2-iodyl-3,5-ditrifluoromethylbenzene sulfonic acid
2-iodyl-3,5,6-trichlorobenzene sulfonic acid
2-iodyl-3-trifluoromethoxybenzene sulfonic acid
2-iodyl-5-cyclohexylbenzene sulfonic acid
2-iodyl-phenol dihydrogen phosphate
2-iodyl-5-methylphenol dihydrogen phosphate
2-iodyl-5-octadecylphenol dihydrogen phosphate
2-iodyl-5-phenylphenol dihydrogen phosphate
2-iodyl-3,5-dimethylphenol dihydrogen phosphate
2-iodyl-3,5-dioctadecylphenol dihydrogen phosphate
2-iodyl-3,5,6-trimethylphenol dihydrogen phosphate
2-iodyl-3,5,6-trioctadecylphenol dihydrogen phosphate
2-iodyl-3,4,5,6-tetramethylphenol dihydrogen phosphate
2-iodyl-3,4,5,6-tetraoctylphenol dihydrogen phosphate
2-iodyl-5-nitrophenol dihydrogen phosphate
2-iodyl-5-chlorophenol dihydrogen phosphate
2-iodyl-5-bromophenol dihydrogen phosphate
2-iodyl-5-methoxyphenol dihydrogen phosphate
2-iodyl-3-octadecyloxyphenol dihydrogen phosphate
2-iodyl-5-hydroxyphenol dihydrogen phosphate
2-iodyl-3,5-dihydroxyphenol dihydrogen phosphate
2-iodyl-5-sulfophenol dihydrogen phosphate 2-iodyl-3,5-disulfophenol dihydrogen phosphate
2-iodyl-5-[2-(2-methoxyethoxy)ethoxy]phenol dihydrogen phosphate
2-iodyl-3,5-dinitrophenol dihydrogen phosphate
2-iodyl-3,5-dichlorophenol dihydrogen phosphate
2-iodyl-3,5-dibromophenol dihydrogen phosphate
2-iodyl-3-iodophenol dihydrogen phosphate
2-iodyl-3,5-diiodophenol dihydrogen phosphate
2-iodyl-5-(2-hydroxyethoxy)phenol dihydrogen phosphate
2-iodyl-5-omega-hydroxypoly(oxyethylene)phenol dihydrogen phosphate
2-iodyl-3,5-diphenylphenol dihydrogen phosphate
2-iodyl-3,5,6-triphenylphenol dihydrogen phosphate
2-iodyl-3-acetylphenol dihydrogen phosphate
2-iodyl-3-octadecanoylphenol dihydrogen phosphate
2-iodyl-5-cyclohexylphenol dihydrogen phosphate
2-iodyl-5-(octadec-7-enyl)phenol dihydrogen phosphate
2-iodyl-3-propargylphenol dihydrogen phosphate
2-iodyl-5-fluorophenol dihydrogen phosphate
2-iodyl-3,5-difluorophenol dihydrogen phosphate
2-iodyl-3,5-ditrifluoromethylphenol dihydrogen phosphate
2-iodyl-3,5,6-trichlorophenol dihydrogen phosphate
2-iodyl-3-trifluoromethoxyphenol dihydrogen phosphate
2-iodyl-N-acetylbenzamide
2-iodyl-5-methyl-N-acetylbenzamide
2-iodyl-5-octadecyl-N-acetylbenzamide
2-iodyl-5-phenyl-N-acetylbenzamide
2-iodyl-3,5-dimethyl-N-acetylbenzamide
2-iodyl-3,5-dioctadecyl-N-acetylbenzamide
2-iodyl-3,5,6-trimethyl-N-acetylbenzamide
2-iodyl-3,5,6-trioctadecyl-N-acetylbenzamide
2-iodyl-3,4,5,6-tetramethyl-N-acetylbenzamide
2-iodyl-3,4,5,6-tetraoctyl-N-acetylbenzamide
2-iodyl-5-nitro-N-acetylbenzamide
2-iodyl-5-chloro-N-acetylbenzamide
2-iodyl-5-bromo-N-acetylbenzamide
2-iodyl-5-methoxy-N-acetylbenzamide
2-iodyl-3-octadecyloxy-N-acetylbenzamide
2-iodyl-5-hydroxy-N-acetylbenzamide
2-iodyl-3,5-dihydroxy-N-acetylbenzamide
2-iodyl-5-sulfo-N-acetylbenzamide
2-iodyl-3,5-disulfo-N-acetylbenzamide
2-iodyl-5-[2-(2-methoxyethoxy)ethoxy]-N-acetylbenzamide
2-iodyl-3,5-dinitro-N-acetylbenzamide
2-iodyl-3,5-dichloro-N-acetylbenzamide
2-iodyl-3,5-dibromo-N-acetylbenzamide
2-iodyl-3-iodo-N-acetylbenzamide
2-iodyl-3,5-diiodo-N-acetylbenzamide
2-iodyl-5-(2-hydroxyethoxy)-N-acetylbenzamide
2-iodyl-5-omega-hydroxypoly(oxyethylene)-N-acetylbenzamide
2-iodyl-3,5-diphenyl-N-acetylbenzamide
2-iodyl-3,5,6-triphenyl-N-acetylbenzamide
2-iodyl-3-acetyl-N-acetylbenzamide
2-iodyl-3-octadecanoyl-N-acetylbenzamide
2-iodyl-5-cyclohexyl-N-acetylbenzamide
2-iodyl-5-(octadec-7-enyl)-N-acetylbenzamide
2-iodyl-3-propargyl-N-acetylbenzamide
2-iodyl-5-fluoro-N-acetylbenzamide
2-iodyl-3,5-difluoro-N-acetylbenzamide
2-iodyl-5-trifluoromethyl-N-acetylbenzamide
2-iodyl-3,5-ditrifluoromethyl-N-acetylbenzamide
2-iodyl-3,5,6-trichloro-N-acetylbenzamide
2-iodyl-3-trifluoromethoxy-N-acetylbenzamide
2-iodyl-N-octadecanoylbenzamide
2-iodyl-5-methyl-N-octadecanoylbenzamide
2-iodyl-5-octadecyl-N-octadecanoylbenzamide
2-iodyl-5-phenyl-N-octadecanoylbenzamide
2-iodyl-3,5-dimethyl-N-octadecanoylbenzamide
2-iodyl-3,5-dioctadecyl-N-octadecanoylbenzamide
2-iodyl-3,5,6-trimethyl-N-octadecanoylbenzamide
2-iodyl-3,5,6-trioctadecyl-N-octadecanoylbenzamide
2-iodyl-3,4,5,6-tetramethyl-N-octadecanoylbenzamide
2-iodyl-3,4,5,6-tetraoctyl-N-octadecanoylbenzamide
2-iodyl-5-nitro-N-octadecanoylbenzamide
2-iodyl-5-chloro-N-octadecanoylbenzamide
2-iodyl-5-bromo-N-octadecanoylbenzamide
2-iodyl-5-methoxy-N-octadecanoylbenzamide
2-iodyl-3-octadecyloxy-N-octadecanoylbenzamide
2-iodyl-5-hydroxy-N-octadecanoylbenzamide
2-iodyl-3,5-dihydroxy-N-octadecanoylbenzamide
2-iodyl-5-sulfo-N-octadecanoylbenzamide
2-iodyl-3,5-disulfo-N-octadecanoylbenzamide
2-iodyl-5-[2-(2-methoxyethoxy)ethoxy]-N-octadecanoylbenzamide
2-iodyl-3,5-dinitro-N-octadecanoylbenzamide
2-iodyl-3,5-dichloro-N-octadecanoylbenzamide
2-iodyl-3,5-dibromo-N-octadecanoylbenzamide
2-iodyl-3-iodo-N-octadecanoylbenzamide
2-iodyl-3,5-diiodo-N-octadecanoylbenzamide
2-iodyl-5-(2-hydroxyethoxy)-N-octadecanoylbenzamide
2-iodyl-5-omega-hydroxypoly(oxyethylene)-N-octadecanoylbenzamide
2-iodyl-3,5-diphenyl-N-octadecanoylbenzamide
2-iodyl-3,5,6-triphenyl-N-octadecanoylbenzamide
2-iodyl-3-acetyl-N-octadecanoylbenzamide
2-iodyl-3-octadecanoyl-N-octadecanoylbenzamide
2-iodyl-5-cyclohexyl-N-octadecanoylbenzamide
2-iodyl-5-(octadec-7-enyl)-N-octadecanoylbenzamide
2-iodyl-3-propargyl-N-octadecanoylbenzamide
2-iodyl-5-fluoro-N-octadecanoylbenzamide
2-iodyl-3,5-difluoro-N-octadecanoylbenzamide
2-iodyl-5-trifluoromethyl-N-octadecanoylbenzamide
2-iodyl-3,5-ditrifluoromethyl-N-octadecanoylbenzamide
2-iodyl-3,5,6-trichloro-N-octadecanoylbenzamide
2-iodyl-3-trifluoromethoxy-N-octadecanoylbenzamide
2-iodylbenzenesulfamide
2-iodyl-5-methylbenzenesulfamide
2-iodyl-5-octadecylbenzenesulfamide
2-iodyl-5-phenylbenzenesulfamide
2-iodyl-3,5-dimethylbenzenesulfamide
2-iodyl-3,5-dioctadecylbenzenesulfamide
2-iodyl-3,5,6-trimethylbenzenesulfamide
2-iodyl-3,5,6-trioctadecylbenzenesulfamide
2-iodyl-3,4,5,6-tetramethylbenzenesulfamide
2-iodyl-3,4,5,6-tetraoctylbenzenesulfamide
2-iodyl-5-nitrobenzenesulfamide
2-iodyl-5-chlorobenzenesulfamide
2-iodyl-5-bromobenzenesulfamide
2-iodyl-5-methoxybenzenesulfamide
2-iodyl-3-octadecyloxybenzenesulfamide
2-iodyl-5-hydroxybenzenesulfamide
2-iodyl-3,5-dihydroxybenzenesulfamide
2-iodyl-5-sulfobenzenesulfamide
2-iodyl-3,5-disulfobenzenesulfamide
2-iodyl-5-[2-(2-methoxyethoxy)ethoxy]benzenesulfamide
2-iodyl-3,5-dinitrobenzenesulfamide
2-iodyl-3,5-dichlorobenzenesulfamide
2-iodyl-3,5-dibromobenzenesulfamide
2-iodyl-3-iodobenzenesulfamide
2-iodyl-3,5-diiodobenzenesulfamide
2-iodyl-5-(2-hydroxyethoxy)-enzenesulfamide
2-iodyl-5-omega-hydroxypoly(oxyethylene)-enzenesulfamide
2-iodyl-3,5-diphenylbenzenesulfamide
2-iodyl-3,5,6-triphenylbenzenesulfamide
2-iodyl-3-acetylbenzenesulfamide
2-iodyl-3-octadecanoylbenzenesulfamide
2-iodyl-5-cyclohexylbenzenesulfamide
2-iodyl-5-(octadec-7-enyl)benzenesulfamide
2-iodyl-3-propargylbenzenesulfamide 2-iodyl-5-fluorobenzenesulfamide
2-iodyl-3,5-difluorobenzenesulfamide
2-iodyl-5-trifluoromethylbenzenesulfamide
2-iodyl-3,5-ditrifluoromethylbenzenesulfamide
2-iodyl-3,5,6-trichlorobenzenesulfamide
2-iodyl-3-trifluoromethoxybenzenesulfamide
2-iodylbenzoic acid
2-iodyl-5-methylbenzoic acid
2-iodyl-5-octadecylbenzoic acid
2-iodyl-5-phenylbenzoic acid
2-iodyl-3,5-dimethylbenzoic acid
2-iodyl-3,5-dioctadecylbenzoic acid
2-iodyl-3,5,6-trimethylbenzoic acid
2-iodyl-3,5,6-trioctadecylbenzoic acid
2-iodyl-3,4,5,6-tetramethylbenzoic acid
2-iodyl-3,4,5,6-tetraoctylbenzoic acid
2-iodyl-5-nitrobenzoic acid
2-iodyl-5-chlorobenzoic acid
2-iodyl-5-bromobenzoic acid
2-iodyl-5-methoxybenzoic acid
2-iodyl-3-octadecyloxybenzoic acid
2-iodyl-5-hydroxybenzoic acid
2-iodyl-3,5-dihydroxybenzoic acid
2-iodyl-5-sulfobenzoic acid
2-iodyl-3,5-disulfobenzoic acid
2-iodyl-5-[2-(2-methoxyethoxy)ethoxy]benzoic acid
2-iodyl-3,5-dinitrobenzoic acid
2-iodyl-3,5-dichlorobenzoic acid
2-iodyl-3,5-dibromobenzoic acid
2-iodyl-3-iodobenzoic acid
2-iodyl-3,5-diiodobenzoic acid
2-iodyl-5-(2-hydroxyethoxy)benzoic acid
2-iodyl-5-omega-hydroxypoly(oxyethylene)benzoic acid
2-iodyl-3,5-diphenylbenzoic acid
2-iodyl-3,5,6-triphenylbenzoic acid
2-iodyl-3-acetylbenzoic acid
2-iodyl-3-octadecanoylbenzoic acid
2-iodyl-5-cyclohexylbenzoic acid
2-iodyl-5-(octadec-7-enyl)benzoic acid
2-iodyl-3-propargylbenzoic acid
2-iodyl-5-fluorobenzoic acid
2-iodyl-3,5-difluorobenzoic acid
2-iodyl-5-trifluoromethylbenzoic acid
2-iodyl-3,5-ditrifluoromethylbenzoic acid
2-iodyl-3,5,6-trichlorobenzoic acid
2-iodyl-3-trifluoromethoxybenzoic acid
2-iodyl-1,4-benzenedicarboxylic acid
2-iodyl-5-methyl-1,4-benzenedicarboxylic acid
2-iodyl-5-octadecyl-1,4-benzenedicarboxylic acid
2-iodyl-5-phenyl-1,4-benzenedicarboxylic acid
2-iodyl-3,5-dimethyl-1,4-benzenedicarboxylic acid
2-iodyl-3,5-dioctadecyl-1,4-benzenedicarboxylic acid
2-iodyl-3,5,6-trimethyl-1,4-benzenedicarboxylic acid
2-iodyl-3,5,6-trioctadecyl-1,4-benzenedicarboxylic acid
2-iodyl-5-nitro-1,4-benzenedicarboxylic acid
2-iodyl-5-chloro-1,4-benzenedicarboxylic acid
2-iodyl-5-bromo-1,4-benzenedicarboxylic acid
2-iodyl-5-methoxy-1,4-benzenedicarboxylic acid
2-iodyl-3-octadecyloxy-1,4-benzenedicarboxylic acid
2-iodyl-5-hydroxy-1,4-benzenedicarboxylic acid
2-iodyl-3,5-dihydroxy-1,4-benzenedicarboxylic acid
2-iodyl-5-sulfo-1,4-benzenedicarboxylic acid
2-iodyl-3,5-disulfo-1,4-benzenedicarboxylic acid
2-iodyl-5-[2-(2-methoxyethoxy)ethoxy]-1,4-benzenedicarboxylic acid
2-iodyl-3,5-dinitro-1,4-benzenedicarboxylic acid
2-iodyl-3,5-dichloro-1,4-benzenedicarboxylic acid
2-iodyl-3,5-dibromo-1,4-benzenedicarboxylic acid
2-iodyl-3-iodo-1,4-benzenedicarboxylic acid
2-iodyl-3,5-diiodo-1,4-benzenedicarboxylic acid
2-iodyl-5-(2-hydroxyethoxy)-1,4-benzenedicarboxylic acid
2-iodyl-5-omega-hydroxypoly(oxyethylene)-1,4-benzenedicarboxylic acid
2-iodyl-3,5-diphenyl-1,4-benzenedicarboxylic acid
2-iodyl-3,5,6-triphenyl-1,4-benzenedicarboxylic acid
2-iodyl-3-acetyl-1,4-benzenedicarboxylic acid
2-iodyl-3-octadecanoyl-1,4-benzenedicarboxylic acid
2-iodyl-5-(octadec-7-enyl)-1,4-benzenedicarboxylic acid
2-iodyl-3-propargyl-1,4-benzenedicarboxylic acid
2-iodyl-5-fluoro-1,4-benzenedicarboxylic acid
2-iodyl-3,5-difluoro-1,4-benzenedicarboxylic acid
2-iodyl-5-trifluoromethyl-1,4-benzenedicarboxylic acid
2-iodyl-3,5-ditrifluoromethyl-1,4-benzenedicarboxylic acid
2-iodyl-3,5,6-trichloro-1,4-benzenedicarboxylic acid
2-iodyl-3-trifluoromethoxy-1,4-benzenedicarboxylic acid
2-iodyl-5-cyclohexyl-1,4-benzenedicarboxylic acid
4-iodyl-1,3-benzenedicarboxylic acid
4-iodyl-5-methyl-1,3-benzenedicarboxylic acid
4-iodyl-5-octadecyl-1,3-benzenedicarboxylic acid
4-iodyl-2,5-dimethyl-1,3-benzenedicarboxylic acid
4-iodyl-2,5-dioctadecyl-1,3-benzenedicarboxylic acid
4-iodyl-2,5,6-trimethyl-1,3-benzenedicarboxylic acid
4-iodyl-2,5,6-trioctadecyl-1,3-benzenedicarboxylic acid
4-iodyl-5-nitro-1,3-benzenedicarboxylic acid
4-iodyl-2,5-dinitro-1,3-benzenedicarboxylic acid
4-iodyl-5-fluoro-1,3-benzenedicarboxylic acid
4-iodyl-2,5-difluoro-1,3-benzenedicarboxylic acid
4-iodyl-5-chloro-1,3-benzenedicarboxylic acid
4-iodyl-2,5-dichloro-1,3-benzenedicarboxylic acid
4-iodyl-5-bromo-1,3-benzenedicarboxylic acid
4-iodyl-2,5-dibromo-1,3-benzenedicarboxylic acid
4-iodyl-5-iodo-1,3-benzenedicarboxylic acid
4-iodyl-2,5-diiodo-1,3-benzenedicarboxylic acid
4-iodyl-5-trifluoromethyl-1,3-benzenedicarboxylic acid
4-iodyl-5-phenyl-1,3-benzenedicarboxylic acid
4-iodyl-2,5-diphenyl-1,3-benzenedicarboxylic acid
4-iodyl-5-methoxy-1,3-benzenedicarboxylic acid
4-iodyl-5-octadecyloxy-1,3-benzenedicarboxylic acid
4-iodyl-5-hydroxy-1,3-benzenedicarboxylic acid
4-iodyl-2,5-dihydroxy-1,3-benzenedicarboxylic acid
4-iodyl-2,5,6-trichloro-1,3-benzenedicarboxylic acid
4-iodyl-5-cyclohexyl-1,3-benzenedicarboxylic acid
2-iodyl-1,3-benzenedicarboxylic acid
2-iodyl-5-methyl-1,3-benzenedicarboxylic acid
2-iodyl-5-octadecyl-1,3-benzenedicarboxylic acid
2-iodyl-5-phenyl-1,3-benzenedicarboxylic acid
2-iodyl-5-cyclohexyl-1,3-benzenedicarboxylic acid
2-iodyl-4,5-dimethyl-1,3-benzenedicarboxylic acid
2-iodyl-4,5-dioctadecyl-1,3-benzenedicarboxylic acid
2-iodyl-5-nitro-1,3-benzenedicarboxylic acid
2-iodyl-4,5-dinitro-1,3-benzenedicarboxylic acid
2-iodyl-5-fluoro-1,3-benzenedicarboxylic acid
2-iodyl-4,5-difluoro-1,3-benzenedicarboxylic acid
2-iodyl-5-chloro-1,3-benzenedicarboxylic acid
2-iodyl-4,5-dichloro-1,3-benzenedicarboxylic acid
2-iodyl-5-bromo-1,3-benzenedicarboxylic acid
2-iodyl-4,5-dibromo-1,3-benzenedicarboxylic acid
2-iodyl-5-iodo-1,3-benzenedicarboxylic acid
2-iodyl-4,5-diiodo-1,3-benzenedicarboxylic acid
2-iodyl-5-sulfo-1,3-benzenedicarboxylic acid
2-iodyl-5-methoxy-1,3-benzenedicarboxylic acid
2-iodyl-octadecyloxy-1,3-benzenedicarboxylic acid
2-iodyl-5-acetyl-1,3-benzenedicarboxylic acid
2-iodyl-5-hydroxy-1,3-benzenedicarboxylic acid
2-iodyl-4,5-diphenyl-1,3-benzenedicarboxylic acid
2-iodyl-4,5-dihydroxy-1,3-benzenedicarboxylic acid
2-iodyl-5-propargyl-1,3-benzenedicarboxylic acid
2-iodylbenzeneacetic acid
2-iodyl-5-methylbenzeneacetic acid
2-iodyl-5-octadecylbenzeneacetic acid
2-iodyl-5-phenylbenzeneacetic acid
2-iodyl-3,5-dimethylbenzeneacetic acid 2-iodyl-3,5-dioctadecylbenzeneacetic acid
2-iodyl-3,5,6-trimethylbenzeneacetic acid
2-iodyl-3,5,6-trioctadecylbenzeneacetic acid
2-iodyl-3,4,5,6-tetramethylbenzeneacetic acid
2-iodyl-3,4,5,6-tetraoctylbenzeneacetic acid
2-iodyl-5-nitrobenzeneacetic acid
2-iodyl-5-chlorobenzeneacetic acid
2-iodyl-5-bromobenzeneacetic acid
2-iodyl-5-methoxybenzeneacetic acid
2-iodyl-3-octadecyloxybenzeneacetic acid
2-iodyl-5-hydroxybenzeneacetic acid
2-iodyl-3,5-dihydroxybenzeneacetic acid
2-iodyl-5-sulfobenzeneacetic acid
2-iodyl-3,5-disulfobenzeneacetic acid
2-iodyl-5-[2-(2-methoxyethoxy)ethoxy]benzeneacetic acid
2-iodyl-3,5-dinitrobenzeneacetic acid
2-iodyl-3,5-dichlorobenzeneacetic acid
2-iodyl-3,5-dibromobenzeneacetic acid
2-iodyl-3-iodobenzeneacetic acid
2-iodyl-3,5-diiodobenzeneacetic acid
2-iodyl-5-(2-hydroxyethoxy)benzeneacetic acid
2-iodyl-5-omega-hydroxypoly(oxyethylene)benzeneacetic acid
2-iodyl-3,5-diphenylbenzeneacetic acid
2-iodyl-3,5,6-triphenylbenzeneacetic acid
2-iodyl-3-acetylbenzeneacetic acid
2-iodyl-5-octadecanoylbenzeneacetic acid
2-iodyl-5-cyclohexylbenzeneacetic acid
2-iodyl-5-(octadec-7-enyl)benzeneacetic acid
2-iodyl-3-propargyl-enzeneacetic acid
2-iodyl-5-fluoro-enzene cetic acid
2-iodyl-3,5-difluorobenzeneacetic acid
2-iodyl-5-trifluoromethylbenzeneacetic acid
2-iodyl-3,5-ditrifluoromethylbenzeneacetic acid
2-iodyl-3,5,6-trichlorobenzeneacetic acid
2-iodyl-3-trifluoromethoxybenzeneacetic acid
2-iodyl-5-cyclohexylbenzeneacetic acid
2-iodyl-1,3-benzenediacetic acid
2-iodyl-5-methyl-1,3-benzenediacetic acid
2-iodyl-5-octadecyl-1,3-benzenediacetic acid
2-iodyl-5-phenyl-1,3-benzenediacetic acid
2-iodyl-5-cyclohexyl-1,3-benzenediacetic acid
2-iodyl-4,5-dimethyl-1,3-benzenediacetic acid
2-iodyl-4,5-dioctadecyl-1,3-benzenediacetic acid
2-iodyl-5-nitro-1,3-benzenediacetic acid
2-iodyl-4,5-dinitro-1,3-benzenediacetic acid
2-iodyl-5-fluoro-1,3-benzenediacetic acid
2-iodyl-4,5-difluoro-1,3-benzenediacetic acid
2-iodyl-5-chloro-1,3-benzenediacetic acid
2-iodyl-4,5-dichloro-1,3-benzenediacetic acid
2-iodyl-5-bromo-1,3-benzenediacetic acid
2-iodyl-4,5-dibromo-1,3-benzenediacetic acid
2-iodyl-5-iodo-1,3-benzenediacetic acid
2-iodyl-4,5-diiodo-1,3-benzenediacetic acid
2-iodyl-5-sulfo-1,3-benzenediacetic acid
2-iodyl-5-methoxy-1,3-benzenediacetic acid
2-iodyl-octadecyloxy-1,3-benzenediacetic acid
2-iodyl-5-acetyl-1,3-benzenediacetic acid
2-iodyl-5-hydroxy-1,3-benzenediacetic acid
2-iodyl-4,5-diphenyl-1,3-benzenediacetic acid
2-iodyl-4,5-dihydroxy-1,3-benzenediacetic acid
2-iodyl-5-propargyl-1,3-benzenediacetic acid
3-iodyl-2-naphthoic acid
3-iodyl-5-methyl-2-naphthoic acid
3-iodyl-5-octadecyl-2-naphthoic acid
3-iodyl-5-phenyl-2-naphthoic acid
3-iodyl-4,5-dimethyl-2-naphthoic acid
3-iodyl-4,5-dioctadecyl-2-naphthoic acid
3-iodyl-4,5,6-trimethyl-2-naphthoic acid
3-iodyl-4,5,6-trioctadecyl-2-naphthoic acid
3-iodyl-4,5,6,8-tetramethyl-2-naphthoic acid
3-iodyl-4,5,6,8-tetraoctyl-2-naphthoic acid
3-iodyl-5-nitro-2-naphthoic acid
3-iodyl-5-chloro-2-naphthoic acid
3-iodyl-5-bromo-2-naphthoic acid
3-iodyl-5-methoxy-2-naphthoic acid
3-iodyl-6-octadecyloxy-2-naphthoic acid
3-iodyl-5-hydroxy-2-naphthoic acid
3-iodyl-6,7-dihydroxy-2-naphthoic acid
3-iodyl-5-sulfo-2-naphthoic acid
3-iodyl-6,7-disulfo-2-naphthoic acid
3-iodyl-5-[2-(2-methoxyethoxy)ethoxy]-2-naphthoic acid
3-iodyl-4,5-dinitro-2-naphthoic acid
3-iodyl-4,5-dichloro-2-naphthoic acid
3-iodyl-4,5-dibromo-2-naphthoic acid
3-iodyl-4-iodo-2-naphthoic acid
3-iodyl-4,5-diiodo-2-naphthoic acid
3-iodyl-5-(2-hydroxyethoxy)-2-naphthoic acid
3-iodyl-5-omega-hydroxypoly(oxyethylene)-2-naphthoic acid
3-iodyl-4,5-diphenyl-2-naphthoic acid
3-iodyl-4,5,6-triphenyl-2-naphthoic acid
3-iodyl-5-acetyl-2-naphthoic acid
3-iodyl-5-octadecanoyl-2-naphthoic acid
3-iodyl-5-cyclohexyl-2-naphthoic acid
3-iodyl-5-(octadec-7-enyl)-2-naphthoic acid
3-iodyl-5-propargyl-2-naphthoic acid
3-iodyl-5-fluoro-2-naphthoic acid
3-iodyl-5,6-difluoro-2-naphthoic acid
3-iodyl-5-trifluoromethyl-2-naphthoic acid
3-iodyl-5,6-ditrifluoromethyl-2-naphthoic acid
3-iodyl-5,6,7-trichloro-2-naphthoic acid
3-iodyl-5-trifluoromethoxy-2-naphthoic acid
[2-(3-carboxy-4-iodylphenoxy)ethyl]triethyl ammonium chloride
N-octyl-3-iodylpyridinium-4-carboxylate
[2-(3-carboxy-4-iodyl phenoxy)ethyl]trimethyl ammonium chloride
cis-3-iodylacrylic acid
trans-2-iodylbut-2-enedioic acid
trans-2-iodylbut-2-enedioic acid monosodium salt
cis-2-chloro-3-iodylacrylic acid
cis-2-sulfo-3-iodylacrylic acid
cis-2-sulfo-3-iodylacrylic acid monosodium salt
trans-2-methyl-3-iodylbut-2-enoic acid
trans-3-iodylbut-2-enoic acid
trans-3-iodylundodec-2-enoic acid
2-[N-methyl-N-(4-hydroxycarbonyl-2-iodyl-1-oxobut-2-ene)]aminoethanesulfonic acid
2-[N-methyl-N-(4-hydroxycarbonyl-2-iodyl-1-oxobut-2-ene)]aminoethanesulfonic acid monosodium salt
2-[N-(4-hydroxycarbonyl-2-iodyl-1-oxobut-2-ene)]aminoethanesulfonic acid
2-[N-(4-hydroxycarbonyl-2-iodyl-1-oxobut-2-ene)]aminoethanesulfonic acid monosodium salt.

It is preferred that the stabilizing compounds have a substituent group such as $C_1$–$C_3$ alkoxy, $C_1$–$C_3$ alkylthio, $CO_2H$, $CO_2M$, $SO_3H$, $OPO_3H$, hydroxy, sulfamoyl, amino, and $C_1$–$C_{10}$ trialkylammonium. Preferred stabilizers are 2-iodosylbenzolic acid; 2-iodosyl-1,4-benzenedicarboxylic acid; 2-iodosyl-1,4-benzenedicarboxylic mono sodium salt; cis-3-iodosylacrylic acid; trans-2-iodosylbut-2-enedioic acid; 2-iodosylbenzoic acid; 2-iodylbenzolic acid; 2-iodyl-1,4-benzenedicarboxylic acid; 2-iodyl-1,4-benzenedicarboxylic mono sodium salt; cis-3-iodylacrylic acid; trans-2-iodylbut-2-enedioic acid; and 2-iodylbenzoic acid.

Suitable monovalent or divalent metal cations include, for example, lithium, sodium, potassium, calcium and the like.

The compositions of the invention are useful as biocides and comprise 3-isothiazolone compound, aqueous solvent, and an effective stabilizing amount of an unsaturated, cyclic iodosyl or iodyl compound sufficient to stabilize the 3-isothiazolone.

Preferred compositions comprise from 0.5 to 90% by weight of one or more 3-isothiazolone compounds, and more preferably from 0.5 to 25% by weight, and even more preferably from 0.5 to 14% by weight.

Preferred compositions comprise from 0.05 to 15% by weight of stabilizer, and more preferably from 0.1 to 10% by weight. The amount of stabilizer used depends on the concentration of 3-isothiazolone. About 2 to 10% stabilizer is used to stabilize 5.1–25% 3-isothiazolone concentrates, and about 0.1 to 7% to stabilize 0.5–5% 3-isothiazolone dilute solutions.

Solvents used to dissolve the 3-isothiazolone compounds may be water or a mixture of water and a water miscible organic solvent which dissolves the 3-isothiazolone. Suitable water miscible organic solvents are glycols, such as ethylene glycol, propylene glycol, diethylene glycol and dipropylene glycol. Water and water/glycol mixtures are preferred.

The compositions of the invention are prepared by mixing the 3-isothiazolone compound, stabilizer, and solvent in any order.

The term microbicide includes bactericides, fungicides, and algaecides. Microbicidal or biocidal activity is intended to include both the inhibition of growth of and elimination of microbial organisms, such as bacteria, fungi, and algae.

Uses of these stabilized microbicides are typically at any locus subject to contamination by bacteria, fungi, yeast or algae. Typically, loci are in aqueous systems such as cooling water systems, laundry rinse water, oil systems such as cutting oils, lubricants, oil fields and the like, where microorganisms need to be killed or where their growth needs to be controlled. However, these stabilized microbicides may also be used in all applications for which known microbicidal compositions are useful; preferred utilities of the compositions of the invention are to protect wood; latex; adhesive; glue; paper; textile; leather; plastics; cardboard; caulking; feed; cosmetics, e.g. shampoos, conditioners, lotions, and creams; and household products, e.g. dish detergents, floor waxes, cleaning products, and the like.

Because isothiazolones are so active as microbicides and only low levels of stabilizer are required to achieve stabilization, the amount of stabilizer in systems being treated will be very low, and therefore it is not likely to interfere with other components in systems requiring protection or with systems to which protected systems will be applied.

It is known in the art that the performance of microbicides may be enhanced by combination with one or more other microbicides. Thus, other known microbicides may be combined advantageously with the composition of this invention.

The 3-isothiazolone used in the following examples was an approximate 3:1 mixture of CMI and MI. All percentages are by weight. Samples were stored at constant temperature (either 40° or 55° C.) in either Dry Baths or an oven. The Dry Baths contained aluminum blocks drilled to accept 7 ml sample vials. Samples were analyzed by HPLC with UV detection after preparation and at various time points after storage.

EXAMPLE 1

The stabilizing effect of 2-iodosylbenzoic acid on the stability of 3-isothiazolones in aqueous solution was determined at varying 3-isothiazolone concentrations.

Eight samples, labeled 1-1 to 1-8, were prepared by dissolving the appropriate amount of 3-isothiazolone in deionized water in a 7 ml glass, screw cap vial. Each sample was spit into two, one half of each sample for storage at 40° C. and the remaining half at 55° C. To each of these split samples, the desired amount of o-iodosylbenzoic acid stabilizer (formula III) was added.

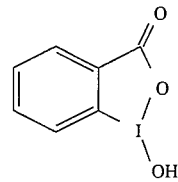

The percentages of 3-isothiazolone and stabilizer in each of the samples are shown below. The samples were then capped, mixed, and placed in a Dry Bath. 2-Iodosylbenzoic acid has a water solubility of about 0.05%, so that in this example this solubility limit is exceeded and the solutions contain a white solid on the bottom of the vial which is the undissolved portion of the stabilizer. During storage, this solid slowly dissolves.

| Sample | % 3-Isothiazolone | % Stabilizer |
|---|---|---|
| 1-1* | 1.0 | 0 |
| 1-2 | 1.0 | 0.1 |
| 1-3* | 5.0 | 0 |
| 1-4 | 5.0 | 0.3 |
| 1-5* | 10.0 | 0 |
| 1-6 | 10.0 | 0.6 |
| 1-7* | 15.0 | 0 |
| 1-8 | 15.0 | 1.2 |

* = Comparative

The samples were analyzed at various time points. Any sample that had less that 50% CMI remaining at a given time point was not analyzed further. "NA" indicates that the sample was not analyzed at that time point. The results, reported in the percentage of CMI remaining, are shown below.

TABLE 1

| | % CMI Remaining after Storage at 40° C. | | | | |
|---|---|---|---|---|---|
| Sample | 2 Days | 7 Days | 14 Days | 35 Days | 49 Days |
| 1-1* | 82 | 37 | 0 | — | — |
| 1-2 | NA | NA | NA | 94 | 98 |
| 1-3* | 96 | 84 | 71 | 29 | — |
| 1-4 | NA | NA | NA | 100 | 100 |
| 1-5* | 94 | 85 | 78 | 43 | — |
| 1-6 | NA | NA | NA | 100 | 100 |
| 1-7* | 88 | 81 | 74 | 29 | — |
| 1-8 | NA | NA | NA | 100 | 100 |

* = Comparative

TABLE 2

| | % CMI Remaining after Storage at 55° C. | | | |
|---|---|---|---|---|
| Sample | 2 Days | 7 Days | 14 Days | 21 Days |
| 1-1* | 0 | — | — | — |
| 1-2 | NA | 95 | 95 | 97 |
| 1-3* | 55 | 0 | — | — |
| 1-4 | NA | 98 | 99 | 0 |
| 1-5* | 64 | 0 | — | — |
| 1-6 | NA | 100 | 100 | 0 |
| 1-7* | 62 | 0 | — | — |
| 1-8 | NA | 100 | 0 | — |

* = Comparative

These data clearly show that 2-iodosylbenzoic acid greatly extends the stability of 3-isothiazolones across a broad range of 3-isothiazolone concentration.

EXAMPLE 2

The effect of pH on the stability of 3-isothiazolones in the presence of 2-iodosylbenzoic acid was determined.

Eight samples, labelled 2-1 to 2-8, were prepared by dissolving the appropriate amount of 3-isothiazolone in deionized water or buffer solution in a 7 ml glass, screw cap vial. Each of the samples 2-1 to 2-8 was split into two, one half for storage at 40° C. and the second half for storage at 55° C. To each of these split samples, the desired amount of 2-iodosylbenzoic acid stabilizer was added. The samples were capped, mixed, and stored at either 40° or 55° C. in a Dry Bath. The 3-isothiazolone concentration in all samples was 5%. Samples 2-1 and 2-2 were prepared with deionized water. All other samples were prepared with buffer. The percentage of stabilizer and the buffer pH used are shown below.

| Sample | % Stabilizer | Buffer pH |
|---|---|---|
| 2-1* | 0 | — |
| 2-2 | 0.4 | — |
| 2-3* | 0 | 4 |
| 2-4 | 0.4 | 4 |
| 2-5* | 0 | 6 |
| 2-6 | 0.4 | 6 |
| 2-7* | 0 | 8 |
| 2-8 | 0.4 | 8 |

The pH 4 buffer was prepared by dissolving 10.2 g of potassium acid phthalate in 1 L of carbon dioxide free deionized water. The pH of the buffer was measured to be 3.98. The pH 6 buffer was prepared by adding 95 ml of a 21 g/L citric acid solution to 405 ml of a 29.4 g/L sodium citrate solution and 500 ml of carbon dioxide free deionized water. The pH of the buffer was measured to be 5.99. The pH 8 buffer was prepared by adding 474 ml of a 28.4 g/L disodium phosphate solution to 26 ml of a 31.2 g/L mono sodium phosphate solution and 500 ml of carbon dioxide free deionized water. The pH of the buffer was measured to be 7.99.

The samples were analyzed at various time points. The results, reported in the percentage of CMI remaining, are shown below.

TABLE 3

| | % CMI Remaining after Storage at 40° C. | | |
|---|---|---|---|
| Sample | 1 Week | 2 Weeks | 3 Weeks |
| 2-1* | 88 | 32 | 21 |
| 2-2 | 99 | 100 | 100 |
| 2-3* | 62 | 0 | — |
| 2-4 | 98 | 93 | 98 |
| 2-5* | 11 | 0 | — |
| 2-6 | 99 | 100 | 88 |
| 2-7* | 48 | 0 | — |
| 2-8 | 91 | 24 | 0 |

* = Comparative

TABLE 4

| | % CMI Remaining after Storage at 55° C. | | |
|---|---|---|---|
| Sample | 1 Week | 2 Weeks | 3 Weeks |
| 2-1* | 0 | — | — |
| 2-2 | 100 | 99 | 97 |
| 2-3* | 0 | — | — |
| 2-4 | 100 | 99 | 40 |
| 2-5* | 0 | — | — |
| 2-6 | 9 | 0 | — |
| 2-7* | 0 | — | — |
| 2-8 | 0 | — | — |

* = Comparative

These data show that 2-iodosylbenzoic acid is a more effective stabilizer for 3-isothiazolones in unbuffered systems than in buffered ones. The data further show that as the buffer increases in pH, the solutions are more difficult to stabilize.

EXAMPLE 3

Four samples, labeled 3-1 to 3-4, containing 5% 3-isothiazolones in deionized water were prepared in 7 ml glass, screw cap vials. To sample 3-2 was added a sufficient amount of 4-iodosylbenzoic acid (formula IV) as stabilizer to give 0.3% by weight (comparative). To Sample 3-3 was added a sufficient amount of 2-iodosylbenzoic acid as stabilizer to give 0.3% by weight. To Sample 3-4 was added a sufficient amount of 2-iodosyl-1,4-benzenedicarboxylic acid (formula V) as stabilizer was added as a 10% aqueous sodium salt to give a 0.3% solution. Sample 3-1 contained no stabilizer. The samples were capped, mixed, and stored at 55° C. in a Dry Bath. The samples were analyzed at various time points. The results, reported in the percentage of CMI remaining, are shown below.

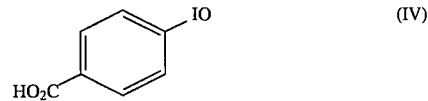

(IV)

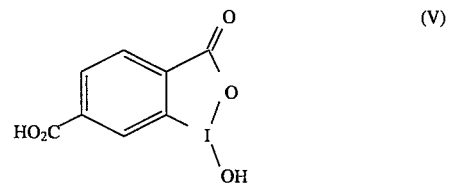

(V)

TABLE 5

| | % CMI Remaining after Storage at 55° C. | | | | | |
|---|---|---|---|---|---|---|
| Sample | 1 Week | 2 Weeks | 3 Weeks | 4 Weeks | 5 Weeks | 9 Weeks |
| 3-1* | 0 | — | — | — | — | — |
| 3-2* | 0 | — | — | — | — | — |
| 3-3 | 100 | 100 | 100 | 100 | 100 | — |
| 3-4 | 96 | 0 | — | — | — | — |

\* = Comparative

These data show that 2-iodosylbenzoic acid and 2-iodosyl-1,4-benzenedicarboxylic acid increased the stability of the 3-isothiazolones.

EXAMPLE 4

Sample 3-4 from Example 3 was observed to form a precipitate on aging. Formation of a precipitate may be disadvantageous in some cases. A way to overcome precipitate formation was investigated.

Six samples, labeled 4-1 to 4-6, containing 5% 3-isothiazolones in deionized water were prepared in 7 ml glass, screw cap vials. Each sample was split into two, one half of each sample to be stored at 40° C. and the remaining half at 55° C. To each of these samples, the desired amount of stabilizer was added. Stabilizer I was 2-iodosylbenzoic acid. Stabilizer II was 2-iodosyl-1,4-benzenedicarboxylic mono sodium salt (formula VI). Sodium citrate was added to samples 4-5 and 4-6 to buffer the solution on the acidic side. The particular stabilizer and amount in each of the samples are shown below. The samples were then capped, mixed and stored at either 40° or 55° C. in a Dry Bath. The pH of the samples was then determined.

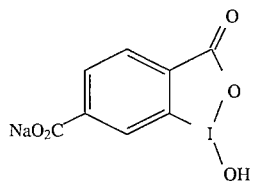

(VI)

TABLE 6

| Sample | % Stabilizer I | % Stabilizer II | % Sodium Citrate | Initial pH |
|---|---|---|---|---|
| 4-1* | 0 | 0 | 0 | 3.27 |
| 4-2* | 0.5 | 0 | 0 | 3.32 |
| 4-3* | 0 | 0.5 | 0 | 4.75 |
| 4-4* | 0 | 1.0 | 0 | 5.24 |
| 4-5 | 0 | 0.5 | 0.5 | 6.68 |
| 4-6 | 0 | 1.0 | 0.3 | 6.52 |

\* = Comparative

The samples were analyzed at various time points. "NA" indicates that the sample was not analyzed at that time point. The results, reported in the percentage of CMI remaining, are shown below.

TABLE 7

| | % CMI Remaining after Storage at 40° C. | | |
|---|---|---|---|
| Sample | 3 Weeks | 4 Weeks | 6 Weeks |
| 4-1* | 27 | 25 | 0 |
| 4-2* | NA | NA | 100 |
| 4-3* | NA | NA | 61 |

TABLE 7-continued

| | % CMI Remaining after Storage at 40° C. | | |
|---|---|---|---|
| Sample | 3 Weeks | 4 Weeks | 6 Weeks |
| 4-4* | NA | NA | 100 |
| 4-5 | NA | NA | 100 |
| 4-6 | NA | NA | 99 |

\* = Comparative

TABLE 8

| | % CMI Remaining after Storage at 55° C. | | | |
|---|---|---|---|---|
| Sample | 1 Week | 2 Weeks | 3 Weeks | 4 Weeks |
| 4-1* | 0 | — | — | — |
| 4-2* | 100 | NA | 100 | 100 |
| 4-3* | 100 | 100 | 100 | 74 |
| 4-4* | 100 | 100 | 100 | 100 |
| 4-5 | 99 | 99 | 99 | 0 |
| 4-6 | 100 | 99 | 99 | 100 |

\* = Comparative

Additionally, the samples that were stored at 40° C. were examined visually at the time the samples were initially prepared (0 weeks) and after 3 weeks storage for the presence of a precipitate. These data are shown in Table 9.

TABLE 9

| | Appearance | |
|---|---|---|
| Sample | Initial | 3 Weeks Storage |
| 4-1* | clear solution | yellow solution |
| 4-2* | crystals** | crystals** |
| 4-3* | clear solution | precipitate |
| 4-4* | " | precipitate |
| 4-5 | " | clear solution |
| 4-6 | " | clear solution |

\* = Comparative
\*\* = Undissolved stabilizer

While samples 4-2 to 4-6 are stable, only samples 4-5 and 4-6 remained precipitate free. By controlling the pH as the samples age, the precipitate of the water insoluble acid (formula V) can be avoided. Also higher amounts of stabilizer extend the period of stability.

EXAMPLE 5

Three samples, labeled 5-1 to 5-3, containing 5% 3-isothiazolones in deionized water were prepared in 7 ml glass, screw cap vials. Sample 5-1 had no stabilizer and was a comparative. Sample 5-2 contained 1% cis-3-iodosylacrylic acid (formula VII) as stabilizer. Sample 5-3 contained 1% trans-2-iodosylbut-2-enedioic acid (formula VIII) as stabilizer. The samples were then capped, mixed and stored at 55° C. in an oven. The samples were anaylzed after 4 and 11 days. The results are reported Table 10.

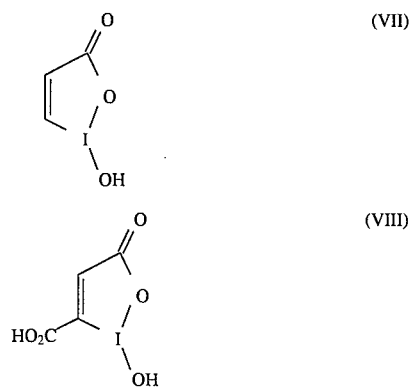

TABLE 10

| | % CMI Remaining at 55° C. | |
|---|---|---|
| Sample | 4 Days | 11 Days |
| 5-1* | 50 | 2 |
| 5-2 | 100 | 95 |
| 5-3 | 100 | 95 |

* = Comparative

The above data show that cis-3-iodosylacrylic acid and trans-2-iodosylbut-2-enedioic acid are effective stabilizers for 3-isothiazolones.

EXAMPLE 6

Two samples, labeled 6-1 and 6-2, containing 5% 3-isothiazolones in deionized water were prepared in 7 ml glass, screw cap vials. Sample 6-1 had no stabilizer and was a comparative. Sample 6-2 contained 1% 2-iodylbenzoic acid (formula IX) as stabilizer. The samples were then capped, mixed and stored at 55° C. in an oven. The samples were anaylzed after 7 and 14 days. The results are reported Table 11.

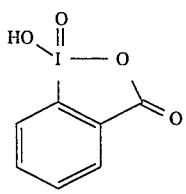

TABLE 11

| | % CMI Remaining | |
|---|---|---|
| Sample | 7 Days | 14 Days |
| 6-1* | 2 | — |
| 6-2 | 103 | 102 |

* = Comparative

The above data show that 2-iodylbenzoic acid is an effective stabilizer for 3-isothiazolones.

EXAMPLE 7—COMPARATIVE

Two samples, labeled 7-1 and 7-2, containing 5% 3-isothiazolones in dipropylene glycol/water (1:1, v/v) were prepared in 7 ml glass, screw cap vials. To sample 7-2 was added a sufficient amount of iodosylbenzene (formula X) as stabilizer to give a 0.3% solution. Sample 7-1 contained no stabilizer. Both samples were split into two and one of each stored at 40° C. and the remaining one of each at 55° C.

The samples were analyzed after 1 week of storage. The results, reported in the percentage of CMI remaining, are shown below.

TABLE 12

| | % CMI Remaining | |
|---|---|---|
| Sample | 1 Week at 40° C. | 1 Week at 55° C. |
| 7-1 | 3 | 0 |
| 7-2 | 7 | 0 |

These data show that iodosylbenzene does not stabilize 3-isothiazolones.

What is claimed is:

1. A composition comprising water, microbicidally active 3-isothiazolone compound, and an effective stabilizing amount of unsaturated, cyclic iodosyl or iodyl compound of formula I and II

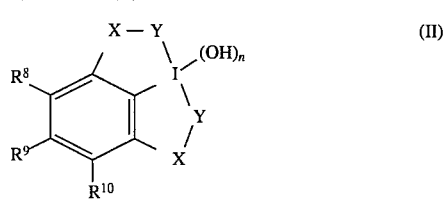

wherein:

X=C(O), $SO_2$, $OPO_3H$, $CH_2C(O)$;

Y=O, $NR^3$;

$R^1$=H, Cl, Br, I, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;

$R^2$=H, Cl, Br, I, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl, $SO_3H$, $CO_2R^4$, $C(O)NR^5R^6$;

$R^1$ and $R^2$ may by joined to form a substituted or unsubstituted 5 or 6 membered ring, optionally fused to another 5 or 6 membered aromatic ring;

$R^3$=H, $C(O)R^7$, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;

$R^4$=H, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl, $(CH_2CH_2)_p$—OH, M;

$R^5$=H, substituted or unsubstituted $C_1$–$C_{18}$ alkyl, $CH_2CH_2SO_3H$, $CH_2CH_2SO_3M$;

$R^6$=H, substituted or unsubstituted $C_1$–$C_{18}$ alkyl;

$R^7$=H, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;

$R^8$, $R^9$, $R^{10}$ are independently selected from the group consisting of CN, OH, $C_1$–$C_4$ alkyl, $C_1$–$C_4$ alkoxy, Cl, Br, F, $NO_2$, $SO_3H$, $SO_3M$, $OCH_2CH_2N^+R^6_3$ $X^-$, $CO_2H$, $CO_2M$, $OPO_3H$;

M=a monovalent or divalent metal cation;

X=halogen;

n=0, 1; and p=1–30.

2. Composition according to claim 1 wherein said 3-isothiazolone is selected from MI, CMI, OI, and mixtures thereof, said 3-isothiazolone(s) being dissolved in said water.

3. Composition according to claim 1 wherein said unsaturated, cyclic iodosyl or iodyl compound is present in an amount greater than its solubility limit so that said composition is incompletely dissolved.

4. Composition according to claim 1 wherein said iodosyl or iodyl compound is the sole stabilizer for said 3-isothiazolone.

5. Composition according to claim 1 further including a water miscible organic solvent.

6. Composition according to claim 1 wherein said 3-isothiazolone comprises about 0.5 to 90% by weight, said iodosyl or iodyl compound comprises 0.05 to 15% by weight, and the balance to make 100% is water or a mixture of water and a water miscible organic solvent.

7. Composition according to claim 1 wherein said iodosyl or iodyl compound is selected from 2-iodosylbenzoic acid; 2-iodosyl-1,4-benzenedicarboxylic acid; 2-iodosyl-1,4-benzenedicarboxylic mono sodium salt; cis-3-iodosylacrylic acid; trans-2-iodosylbut-2-enedioic acid; 2-iodosylbenzoic acid; 2-iodylbenzoic acid; 2-iodyl-1,4-benzenedicarboxylic acid; 2-iodyl-1,4-benzenedicarboxylic mono sodium salt; cis-3-iodylacrylic acid; trans-2-iodylbut-2-enedioic acid; and 2-iodylbenzoic acid.

8. Composition according to claim 7 wherein said iodosyl or iodyl compound is 2-iodosylbenzoic acid and said 3-isothiazolone is 5-chloro-2-methyl-4-isothiazolin-3-one.

9. Method of stabilizing a microbicidally active 3-isothiazolone in a water solution comprising introducing an effective stabilizing amount of unsaturated, cyclic iodosyl or iodyl compound of formula I and II

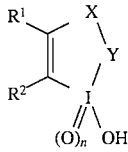
(I)

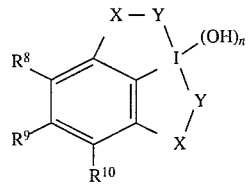
(II)

wherein:

X=C(O), $SO_2$, $OPO_3H$, $CH_2C(O)$;

Y=O, $NR^3$;

$R^1$=H, Cl, Br, I, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;

$R^2$=H, Cl, Br, I, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl, $SO_3H$, $CO_2R^4$, $C(O)NR^5R^6$;

$R^1$ and $R^2$ may by joined to form a substituted or unsubstituted 5 or 6 membered ring, optionally fused to another 5 or 6 membered aromatic ring;

$R^3$=H, $C(O)R^7$, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;

$R^4$=H, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl, $(CH_2CH_2)_p$—OH, M;

$R^5$=H, substituted or unsubstituted $C_1$–$C_{18}$ alkyl, $CH_2CH_2SO_3H$, $CH_2CH_2SO_3M$;

$R^6$=H, substituted or unsubstituted $C_1$–$C_{18}$ alkyl;

$R^7$=H, substituted or unsubstituted $C_1$–$C_{18}$ alkyl, substituted or unsubstituted $C_2$–$C_{18}$ alkenyl, substituted or unsubstituted $C_4$–$C_6$ aryl, substituted or unsubstituted $C_7$–$C_{10}$ aralkyl;

$R^8$, $R^9$, $R^{10}$ are independently selected from the group consisting of CN, OH, $C_1$–$C_4$ alkyl, $C_1$–$C_4$ alkoxy, Cl, Br, F, $NO_2$, $SO_3H$, $SO_3M$, $OCH_2CH_2N^+R^6_3$ $X^-$, $CO_2H$, $CO_2M$, $OPO_3H$;

M=a monovalent or divalent metal cation;

X=halogen;

n=0, 1; and p=1–30.

* * * * *